US008546126B2

(12) United States Patent
Goedegebuur et al.

(10) Patent No.: US 8,546,126 B2
(45) Date of Patent: Oct. 1, 2013

(54) OVER EXPRESSION OF FOLDASES AND CHAPERONES IMPROVES PROTEIN PRODUCTION

(75) Inventors: Frits Goedegebuur, Vlaardingen (NL); Paulien Neefe-Kruithof, Zoetermeer (NL); Jeffrey P. Pucci, Pacifica, CA (US); Michael Ward, San Francisco, CA (US)

(73) Assignee: Danisco US Inc., Palo Alto, CA (US)

( * ) Notice: Subject to any disclaimer, the term of this patent is extended or adjusted under 35 U.S.C. 154(b) by 691 days.

(21) Appl. No.: 12/531,030

(22) PCT Filed: Mar. 21, 2008

(86) PCT No.: PCT/US2008/003802

§ 371 (c)(1),
(2), (4) Date: Jan. 27, 2010

(87) PCT Pub. No.: WO2008/115596

PCT Pub. Date: Sep. 25, 2008

(65) Prior Publication Data

US 2010/0144013 A1 Jun. 10, 2010

Related U.S. Application Data

(60) Provisional application No. 60/919,332, filed on Mar. 21, 2007.

(51) Int. Cl.
*C12N 1/15* (2006.01)
*C12P 1/00* (2006.01)

(52) U.S. Cl.
USPC .................................... 435/254.11; 435/71.1

(58) Field of Classification Search
None
See application file for complete search history.

(56) References Cited

U.S. PATENT DOCUMENTS

| | | | | |
|---|---|---|---|---|
| 2004/0186070 | A1 | 9/2004 | Penttila et al. | |
| 2005/0158825 | A1* | 7/2005 | Power et al. | 435/69.1 |
| 2008/0057538 | A1* | 3/2008 | Belyaev | 435/69.1 |

OTHER PUBLICATIONS

Valkonen, M. Functional studies of the secretory pathway of filamentous fungi. VTT Publications 505: 1-118, 2003.*

Cheo et al. Concerted assembly and cloning of multiple DNA segments using in vitro site-specific recombination: functional analysis of multi-segment expression clones. Genome Res. Oct. 2004;14(10B):2111-20.*

Cardoza et al. Expression of a synthetic copy of the bovine chymosin gene in *Aspergillus awamori* from constitutive and pH-regulated promoters and secretion using two different pre-pro sequences. Biotechnol Bioeng. Aug. 5, 2003;83(3):249-59.*

Barreau, C. et al. "Use of a Linear Plasmid Containing Telomeres as an Efficient Vector for Direct Cloning in The Filamentous Fungus*Podospora anserina*." *Fungal Genetics and Biology* 25(1):22-30, 1998.

Conesa, A. et al. "The Secretion Pathway in Filamentous Fungi: A Biotechnological View." *Fungal Genetics and Biology* 33(3):155-171, 2001.

Database Genbank. "*Trichoderma reesei* cbh1 gene for cellobiohydrolase I, upstream region." Accession No. D86235, 1997.

Dunn-Coleman, N.S. et al. "Commercial levels of chymosin production by *Aspergillus*." *Bio/Technology* (*Nature Publishing Company*) 9(10):976-981, 1991.

Graessle, S. et al. "Regulated system for heterologous gene expression in *Penicillium chrysogenum*." *Appl. Environ. Microbiol.* 63(2):753-756, 1997.

Harmsen, M.M. et al. "Overexpression of binding protein and disruption of the PMR1 gene synergistically stimulate secretion of bovine prochymosin but not plant Thaumatin in yeast." *Applied Microbiology and Biotechnology* 46(4):365-370, 1996.

Leuker, C.E. et al. "Sequence and promoter regulation of the PCK1 gene encoding phosphoenolpyruvate carboxykinase of the fungal pathogen *Candida albicans*." *Gene* 192(2):235-240, 1997.

Liu, M. et al. "Conserved Fungal Genes as Potential Targets for Broad-Spectrum Antifungal Drug Discovery." *Eukaryotic Cell* 5(4):638-649, 2006.

Lombrana, M. et al. "Modulation of *Aspergillus awamori* Thaumatin Secretion by Modification of bipA Gene Expression." *Appl. Environ. Microbiol.* 70(9):5145-5152, 2004.

Munro, C.A. et al. "Chs1 of *Candida albicans* is an essential chitin synthase required for synthesis of the septum and for cell integrity." *Molecular Microbiology* 39(5):1414-1426, 2001.

Rawlings, N.D. et al. "MEROPS: the peptidase database." *Nucl. Acids Res.* 34(Suppl. 1):D270-272, 2006.

Sheir-Neiss, G. et al. "Characterization of the secreted cellulases of *Trichoderma reesei* wild type and mutants during controlled fermentations." *Applied Microbiology and Biotechnology* 20(1):46-53, 1984.

Ståhlberg, J. et al. "Activity Studies and Crystal Structures of Catalytically Deficient Mutants of Cellobiohydrolase I from*Trichoderma reesei*." *Journal of Molecular Biology* 264(2):337-349, 1996.

Yanisch-Perron, C. et al. "Improved M13 phage cloning vectors and host strains: nucleotide sequences of the M13mp18 and pUC19 vectors." *Gene* 33(1):103-119, 1985.

* cited by examiner

*Primary Examiner* — Michele K Joike
(74) *Attorney, Agent, or Firm* — Danisco US Inc.

(57) ABSTRACT

The present teachings provide methods for increasing protein secretion, e.g., chymosin in filamentous fungi by co-expressing certain chaperone(s) and/or foldase(s). The present teachings also provide filamentous fungi containing certain chaperone(s) and/or foldase(s) and a protein of interest for increased secretion.

11 Claims, 5 Drawing Sheets actagtgccgagatcacccgcatccctctctacaagggcaagagcctccgcaaggccctcaaggagcacggcctcctcgaggacttcctccagaagcagcagtacggcatcagcag
caagtacagcggcttcggcgaggtcgccagcgtccctctcaccaactacctcgacagccagtacttcggcaagatctacctcggcacccctcctcaggagttcaccgtcctcttcgacacc
ggcagcagcgacttctgggtcccgagcatctactgcaagagcaacgcctgcaagaaccaccagcgcttcgaccctcgcaagagcagcaccttccagaacctcggcaagcctctcag
catccactacggcaccggcagcatgcagggcatcctcggctacgacaccgtcacggtctccaacatcgtcgacatccagcagactgtcggcctcagcacccaggagcctggcgacgt
ctttacctacgccgagttcgacggcatcctgggcatggcctaccctagcctcgccagcgagtacagcatccctgtctttgacaacatgatgaaccgccacctcgtcgcccaggacctcttca
gcgtctacatggaccgcaacggccaagagagcatgctcaccctcggcgccatcgaccctagctactacaccggcagcctccactgggtcccggtcaccgtccagcagtactggcagtt
caccgtcgacagcgtcaccatcagcggcgtcgtcgtcgcctgcgagggcggctgccaggccatcctggacaccggcaccagcaagctcgtcggccctagcagcgacatcctgaacat
ccagcaggccatcggcgccacccagaaccagtacggcgagttcgacatcgactgcgacaacctcagctacatgcctaccgtcgtctttgagatcaacggcaagatgtaccctctcacc
cctagcgcctacaccagccaggaccagggcttctgcaccagcggcttccagagcgagaaccacagccagaagtggatcctcggcgacgtctttatccgcgagtactacagcgtctttga
ccgcgccaacaacctcgtcggcctcgccaaggccatctaaggcgcgccg

Figure 2 mRNA levels in *T. reesei* production strains after 72 hrs of fermentation in shake flask.

SEQUENCE LISTING

<160> NUMBER OF SEQ ID NOS: 42

<210> SEQ ID NO 1
<211> LENGTH: 2267
<212> TYPE: DNA
<213> ORGANISM: Trichoderma reesei

<400> SEQUENCE: 1

```
atggctcgtt cacggagctc cctggccctc gggctgggcc tgctctgctg gatcacgctg      60
ctcttcgctc ctctggcgtt tgtcggaaag gccaatgccg cgagcgacga cgcggacaac     120
tacggcactg ttatcggaat tgtaagtcga ctgacggcag caaccccgcc attttcttgg     180
tgttgatgct caggcagccc tgctaacacg cttctcctcc gcccaggatc tcggaactac     240
ctacagctgc gtcggtgtga tgcagaaggg caaggttgag attctcgtca acgaccaggg     300
taaccgaatc actccctcct acgtggcctt taccgacgag gagcgtctgg ttggcgattc     360
cgccaagaac caggccgccg ccaaccccac caacaccgtc tacgatgtca agtcagttct     420
accgccctgt tggcttctat tgtataagtg gacaattagc taactgttgt cacaggcgat     480
tgattggccg caaattcgac gagaaggaga tccaggccga catcaagcac ttcccctaca     540
aggtcattga gaagaacggc aagcccgtcg tccaggtcca ggtcaacggc cagaagaagc     600
agttcactcc cgaggagatt tctgccatga ttcttggcaa gatgaaggag gttgccgagt     660
cgtacctggg caagaaggtt acccacgccg tcgtcaccgt ccctgcctac ttcaacgtga     720
gtcttttccc cgaaattcct cgaggattcc aagagccatc tgctaacagc ccgataggac     780
aaccagcgac aggccaccaa ggacgccggt accattgccg gcttgaacgt tctccgaatc     840
gtcaacgaac ccaccgctgc cgctatcgcc tatggtctgg acaagaccga cggtgagcgc     900
cagatcattg tctacgatct cggtggtggt acctttgatg tttctctcct gtccattgac     960
aatggcgtct tcgaggtctt ggctaccgcc ggtgacaccc accttggtgg tgaggacttt    1020
gaccagcgca ttatcaacta cctggccaag gcctacaaca agaagaacaa cgtcgacatc    1080
tccaaggacc tcaaggccat gggcaagctc aagcgtgaag ccgaaaaggc caagcgtacc    1140
ctctcttccc agatgagcac tcgtatcgaa atcgaggcct tcttcgaggg caacgacttc    1200
tccgagactc tcacccgggc caagttcgag gagctcaaca tggacctctt caagaagacc    1260
ctgaagcctg tcgagcaggt tctcaaggac gccaacgtca agaagagcga ggttgacgac    1320
atcgttctgg tcggcggttc cacccgtatc cccaaggttc agtctcttat cgaggagtac    1380
tttaacggca agaaggcttc caagggtatc aaccccgacg aggctgttgc tttcggtgcc    1440
gccgtccagg ccggtgtcct ttctggtgag gaaggtaccg atgacattgt tctcatggac    1500
gtcaaccccc tgactctcgg tatcgagacc actggcggag tcatgaccaa gctcattccc    1560
cgcaacaccc ccatccccac tcgcaagagc cagatcttct cgactgctgc cgataaccag    1620
cccgtcgtcc tgatccaggt cttcgagggt gagcgttcca tgaccaagga caacaacctc    1680
ctgggcaagt tcgagcttac cggcattcct cctgcccccc gcggtgtccc ccagattgag    1740
gtttccttcg agttggatgc caacggtatc ctcaaggtct ccgctcacga caagggcacc    1800
ggcaagcagg agtccatcac catcaccaac gacaagggcc gtctcaccca ggaggagatt    1860
gaccgcatgg ttgccgaggc cgagaagttc gccgaggagg acaaggctac ccgtgagcgc    1920
atcgaggccc gtaacggtct tgagaactac gccttcagcc tgaagaacca ggtcaatgac    1980
gaggagggcc tcggcggcaa gattgacgag gaggacaagg agactgtaag ttgaagcgat    2040
```

```
ccatcactgc tttctgatgc ggacatgtca cactaacact tgaccagatt cttgacgccg   2100

tcaaggaggc taccgagtgg ctcgaggaga acggcgccga cgccactacc gaggactttg   2160

aggagcagaa ggagaagctg tccaacgtcg cctaccccat cacctccaag atgtaccagg   2220

gtgctggtgg ctccgaggac gatggcgact tccacgacga attgtaa                 2267


<210> SEQ ID NO 2
<211> LENGTH: 1942
<212> TYPE: DNA
<213> ORGANISM: Trichoderma reesei

<400> SEQUENCE: 2

atgaagttca acaccgtcgc ggccgctgcg gctctgctcg ctggtgtcgc gtatgccgag     60

gacgtcgagg agtccaaggc agtcccggag cttcccacct ttactgtgag tttgccctct    120

ctttcatctt tggaaaagga cccaaatgtt ggcgcttggc tccagcttgg agcaagcttc    180

ttggacgacg ggatatcatg aaccgctgct gacagttccc accaatcgct tagcccacct    240

ccatcaaggc ggacttcctc gagcagttca ccgacgactg ggagtcccgg tggaagcctt    300

cccacgccaa gaaggacacc agcggctccg acaaggacgc agaggaggaa tgggcctacg    360

tcggcgagtg ggcggtcgag gagccctacc agtacaaggg catcaacggc gacaagggcc    420

tcgttgtcaa gaaccctgcc gcgcaccacg ccatctcggc caagttcccc aagaagattg    480

acaacaaggg caagacgctc gtcgtgcagt acgaggtgaa gctccagagt aagtttggcc    540

tctgcaactc ccccgtgata accaaagcga gatgtggaca ttgtgctgac ctatacgctt    600

ccagagggac tggactgcgg cggtgcctac atgaagctgc tgcgcgacaa caaggctctc    660

caccaggatg agttcagcaa caccaccccc tacgtcatca tgtttggccc cgacaagtgc    720

ggccacaaca accgggtcca cttcatcgtc aaccacaaga accccaagac tggcgagtac    780

gaggagaagc acctcaactc ggccccggcc gtcaacattg tcaagacgac ggagctctac    840

accctcattg tccaccccaa caacaccttc tccatcaagc agaacggtgt cgagaccaag    900

gccggcagcc ttctcgagga cctgagccct cccatcaacc ctcccaagga gattgatgac    960

cccaaggact ccaagcccga cgactgggtc gacgaggctc gcattcccga ccccgaggcc   1020

gtcaagcccg aggactggga cgaggatgcg ccctttgaga ttgtcgacga ggaggccgtc   1080

aagcccgagg actggctcga ggacgagccc accacgatcc ccgaccccga ggcccagaag   1140

cccgaggact gggatgacga ggaggacggc gactggatcc ctcccaccgt ccccaacccc   1200

aagtgcgagg acgtctccgg ttgcggcccc tggaccaagc ccatggtcag gaaccccaac   1260

tacaagggca agtggactgc tccttacatt gacaaccctg cctacaaggg cgtctgggct   1320

ccccgcaaga tcaagaaccc cgactacttt gaggacaaga cgcccgccaa ctttgagccc   1380

atgggagctg taagtttcgt tcctttacca agaccttcat gacgctcgat tgctaaccag   1440

tgctcgacag attggcttcg agatctggac catgaccaac gacatcctct ttgacaacat   1500

ctacattggc cactccattg aggatgccga gaagctggcc aacgagacct tcttcgtcaa   1560

gcaccccatt gagaaggcgc ttgccgaggc tgatgagccc aagtttgacg acaccccccaa  1620

gtcgccctct gacctcaagt tcctcgacga ccccgtgacc tttgtcaagg agaagcttga   1680

cctgttcctg accattgccc agcgcgaccc cgttgaggcc atcaagtttg ttcccgaggt   1740

cgccggtggc attgccgccg tcttcgtcac cctgattgcc atcattgtcg gtctggtcgg   1800

ccttggctcc tcatcggccg cccccaagaa ggccgccgcc actgctaagg agaaggccaa   1860

ggacgtttcc gaggctgttg caagcggtgc cgacaaggtc aagggagagg ttaccaagcg   1920
```

aaccacccgc agccagtcgt ag 1942

<210> SEQ ID NO 3
<211> LENGTH: 1910
<212> TYPE: DNA
<213> ORGANISM: Trichoderma reesei

<400> SEQUENCE: 3
atgaagtcgg cgagcaaatt gttctttctc tccgtgtttt ccctatgggc gacgccgggc 60
gcatgctcaa gctcgtcaag tacatgcact gtacgtcaac ccaaccttgg cctcgtttcc 120
cctttggaag aatgctttgc gctgacagat tttgttgatc tagttctccc caaacgccat 180
cattgacgat ggatgcgttt cgtatgcgac tctcgataga ctcaatgtca aggtgaagcc 240
tgctatagac gaactcgttc agacgaccga cttcttttcg cactatcgct tgaacctctt 300
caacaaaaaa tgccccttct ggaacgacga agatggcatg tgcggtaaca ttgcctgcgc 360
cgtcgagacg ctggacaacg aagaagatat tcccgagata tggagggctc acgagcttag 420
caagctggaa ggccctcgag cgaagcatcc cggcaagcaa gagcagaggc agaaccctga 480
gcgaccgctg cagggagagc tgggggagga tgtaggggag agctgcgtgg ttgaatacga 540
cgacgagtgt gacgacagag actactgcgt ctgggacgac gaaggcgcaa cgtccaaggg 600
ggactacatc agcttgttgc gcaaccccga gcgcttcacc ggctatggcg gtcaaagtgc 660
aaagcaggtg tgggacgcca tctactcgga gaactgcttc aagaagagct cgtttcccaa 720
gtcggccgat ctaggcgtct cgcaccgccc aaccgaggcg gctgctctgg acttcaagca 780
ggtcctggac accgctggcc gccaggctca actggaacag cagcggcaga gcaacccaaa 840
cattcccttt gttgccaaca ctggctacga ggtggacgat gagtgtctgg agaagcgcgt 900
gttctaccgg gtggtgtcgg gaatgcacgc cagcatcagc gtccacctgt gctgggactt 960
cctgaaccag agcacggggc aatggcagcc caacttggac tgctacgaga gccgcctgca 1020
caagtttcca gaccgcatca gcaacctcta cttcaactac gctctcgtga ctcgcgccat 1080
tgcgaagctg ggcccgtatg tactgtcacc gcagtacacc ttttgcacag ggacccgtt 1140 gcaagaccag gagacgcgag acaagattgc ggccgtcacg aagcacgcgg ctagcgtccc 1200
gcagatcttt gacgagggcg tcatgtttgt caacggcgaa ggcccctcgc tcaaggaaga 1260
tttccgcaat cgcttccgca acatcagccg ggtcatggac tgcgtcggct gcgacaagtg 1320
ccgtctctgg ggcaagatcc agaccagcgg ctacggcacg gctttgaaga ttctgtttga 1380
gttcaacgag ggccagaagc cgccgcccct caagaggacc gagctggtgg ccctcttcaa 1440
cacgtatgcc agactcagct cgtcggtggc ggccgttggg cgattcaggg ccatgattga 1500
catgcgcgac aagatggcgt ccaagcccga cttcaagccc gaggatctct acacgctcat 1560
cgacgaggcg gacgaggaca tggacgagtt tatcaggatg caaaatcgtg ggagccacgg 1620
agatacgctg ggcgagcagg tcggaaacga atttgcccgc gtcatgatgg ccgtcaagat 1680
tgtgctcaag agttggatcc gaacgcccaa gatgatgtaa gtctcttctc tcttttttt 1740 ccccttcttc gagtggcaca aagctcttca ttgagatgga ctaacacaat tctagttggc 1800
aaattgtctc ggaagagacg tcgagattgt atcgcgcttg ggtcggtctg cctgcgcgac 1860
ccagacggta cgcgttcaga ctgcccaact tgaatagaga cgagttgtga 1910

<210> SEQ ID NO 4
<211> LENGTH: 3027
<212> TYPE: DNA
<213> ORGANISM: Trichoderma reesei

<400> SEQUENCE: 4

```
atgaagtcac cgaggaaatc accgttgctg aagctcctcg gagccgcctt tctcttctcc     60
accaacgttc tcgccatctc cgctgttctc ggagtcgatc tgggaaccga gtacatcaag    120
gcggcgctgg tgaagcccgg catcccgctt gagattgtgc tcacgaaaga ttcccgacga    180
aaagaaacct cggccgtcgc cttcaagccg gcaaagggcg ccttaccgga gggccagtac    240
cccgaacgga gctatggcgc cgacgcaatg gcactcgccg cacgattccc cggcgaagta    300
tacccgaatc tgaagcccct gcttggactg ccagtggggg atgccattgt ccaagaatat    360
gcggccaggc accctgcgtt gaagctacag gcgcacccca cgcggggaac tgctgcgttc    420
aagacggaga cgctgtctcc ggaagaggag gcttggatgg tggaggagct gttggccatg    480
gagcttcaga gcatccagaa gaacgcagag gttaccgctg gcggcgactc ttcgatacgc    540
tccatcgtgc tcaccgtccc gccgttttac accatcgagg agaagcgagc cctgcagatg    600
gcagcagagc tcgccggctt caaggtcctg agccttgtca gcgacggact ggccgtgggc    660
ctcaactatg ccaccagtcg ccaattcccg aatatcaacg aaggcgccaa gccggaatac    720
cacttggtct ttgacatggg agcgggctcc acaactgcta cggtcatgag gttccaaagc    780
cgtacggtta aggacgtcgg caagttcaac aagacggttc aggagatcca ggttctcggc    840
agcggctggg acaggaccct cggaggagac tctctcaact cgctaatcat cgatgacatg    900
attgctcagt ttgtggaatc caagggtgct cagaagattt cggcaaccgc cgagcaggtt    960
cagtctcatg gccgcgccgt tgcaaagctg agcaaggaag ccgagcgtct ccgacacgtc   1020
ctcagcgcca accagaacac ccaagccagc tttgagggac tgtacgaaga tgttgacttc   1080
aagtacaaga tctctcgggc tgacttcgag accatggcaa aggctcatgt cgagcgagtc   1140
aacgctgcca tcaaggacgc tctgaaggcc gcgaacctcg agattggcga tctgacttcc   1200
gtcattcttc acggtggtgc gacccgtact ccgtttgtgc gagaggccat tgagaaagct   1260
cttggttctg gcgacaagat ccgtaccaat gtcaactctg atgaggcagc cgtctttggt   1320
gctgctttcc gggctgctga gctcagccca agcttccgtg tgaaggagat taggatttct   1380
gagggtgcaa actacgcagc tggcattact tggaaggctg cgaacggcaa ggtacaccgc   1440
caacgactct ggactgcccc gtcgccgctc ggtggcccgg ccaaggagat tacctttacg   1500
gaacaggagg actttactgg tttattctat caacaagttg acactgagga taagcccgtc   1560
aagtcgttct cgactaagaa ccttaccgcc tctgttgctg ctctgaaaga aaagtatccc   1620
acttgtgccg atactggcgt tcagttcaag gctgccgcga agctccgtac cgagaacggc   1680
gaggttgcca tcgtcaaggc ctttgtggag tgcgaggctg aagtcgttga gaaggaaggc   1740
tttgttgacg gcgttaagaa cctctttggc ttcgggaaga aagatcagaa gcccctcgcc   1800
gaaggaggag acaaggacag tgccgatgcg tctgcggatt ctgaggccga gacggaggaa   1860
gctagctctg cgacaaagtc ctcctcttcc accagcacca ccaagtccgg agatgctgcc   1920
gagtcaacag aggctgcaaa ggaagtcaag aagaagcagc ttgtttctat ccctgtcgaa   1980
gtcacgttgg aaaaggctgg aatccctcag cttaccaagg ccgagtggac caaggccaag   2040
gatcgactga aggcattcgc cgcctccgac aaggccaggc tgcagcgcga agaggccctg   2100
aaccagctcg aagcattcac ttacaaggtt cgcgaccttg tcgacaacga agccttcatc   2160
tccgcgtcta ccgaggcgga gcgacagacg ctctctgaaa aggctagcga agcaagtgac   2220
tggctttatg aggagggcga ctcggccacg aaagatgact ttgttgctaa gctcaaggct   2280
ctgcaagatc tcgtggcacc gatccagaac cgcctggacg aggctgagaa gcggcctggt   2340
```

ctgattagcg atctgagaaa cattctcaac accacaaatg tgtttattga cactgttcgt 2400
gggcagattg ctgcgtatga tgaatggaaa tccacagctt cagccaagtc ggctgaatca 2460
gccacctcga gtgctgccgc cgaggcgacg accaacgact ttgaagggct cgaggatgag 2520
gacgacagcc ccaaagaggc tgaggagaag cccgttccag aaaaggtcgt gcccccgctg 2580
cacaactctg aggagattga cacgctcgag gttctctaca aggagactct ggagtggctg 2640
aacaagctcg aacgccaaca ggcagatgtt cctctcaccg aagagcccgt gcttgttgtc 2700
agcgagctgg ttgccagacg agatgcgctt gacaaggcca gcttagacct cgcgctgaag 2760
agctacaccc aataccagaa gaacaagccc aagaagccca ccaagagcaa gaaggcgaag 2820
aagcaggaca agacgaagag cgccgacaag gctggcccga cgtttgagtt tcccgagggc 2880
agcgtgcccc tctccggcga ggagctggag gagctggtca agaagtacat gaaggaggag 2940
gaggagaccc gcaggcaggc cgagggcgga caggcagagg agaagccggc ggaagataca 3000
gagaagtcga gccatgacga gctctaa 3027

<210> SEQ ID NO 5
<211> LENGTH: 1417
<212> TYPE: DNA
<213> ORGANISM: Trichoderma reesei

<400> SEQUENCE: 5
atggtagcca gattgtccag catctacgcc tgtgggctct tagcctggac gcacattgtt 60
tgcgcctctc agtttagcga cccgatgcaa ctacagaagc atcttgcaca gaatgactat 120
actttaattg cttgtaagtc atgacaatat cgccttctaa agtgtgtcaa ctcaggtaga 180
aataattgct aatagtagct tacagttgtt gctgtaagag ttgttcgggt caatatctta 240
cctagtcaag tcgagactcg aggctgacct taaggtatcg ctaccactta cagcctcaac 300
tgtaagtttt ggccaggcca agtttgaacc catctccctt aagaacaccg aacttaaaaa 360
aagtcaaacg gcagagaagc cagcaaactc ctcttagaag aatggcagac ggtccagcaa 420
catgtcgcct ccaccgccac catcgactgt ccgtccagcc ctaaactctg tcaggagatg 480
gacgtcgcct cctttcccgc tattcggctc taccgccagg atggctcagt aacacgttat 540
cgagggcctc gtcggaccgc accgtgagtt gacactttct tcgaattttg gagttaatct 600
ctcaaagcat gaagtgactg actgactacc ttacctccca ggatcgacgc ctttgtgaag 660
cgtgctctca aaccatccgt gcagaatgtt cctgggcagc aacttgccaa cttcatcacc 720
aacgacgact atgtattcat cgccaagctg caaggcgaga gcgagagcat caattctcac 780
tacagggatt ttgcgcaaga gtattctgat cgatactcgt ttggcatcat cacgagtggc 840
tctgtaccct ccaatggcgt ctggtgctac aacaacgtcg acggaaatca gcacgcggcg 900
acggacttga acgatccaaa tgccttgaag aagcttctca atctttgcac cgcggaggtc 960
attccccagc ttacacgacg caatgagatg acttatcttt ccgtatgtct tctgttctcc 1020
ctcctcactt ttaaaatgtt cagtagaaga agcttgggct tctgacccct tattccagtc 1080
aggccgatcc ttggtctatt acttctccaa caatgaagca gaccgcgaag catacgtcaa 1140
agcgctcaaa cccatcgccc agcgatacgc cgagttcctc cagttcgtca ccgtcgactc 1200
tggcgagtat cccgatatgc tgcgcaatct gggcgttcgc tccgccggag gcctggcagt 1260
gcaaaacgtc cacaacggac atattttccc cttcagagga gacgctgctg cttcgcctgg 1320
acaggttgac cagttcattg tggccatctc agaaggtagg gcgcagcctt gggatgggag 1380
gtttgacgag ggacaggagg cgcatgatga gctctga 1417

<210> SEQ ID NO 6
<211> LENGTH: 2174
<212> TYPE: DNA
<213> ORGANISM: Trichoderma reesei

<400> SEQUENCE: 6
atgcggctaa catccttctt ctctggcctg gccgcctttg gccttctgtc atctccagca 60
ctggcagatg atgaagctga caacgtcccc gcgcccacat acttcgattc cgtcatggtg 120
cctcccttga cagaactaac gccagacaac ttcgaaaagg aggcaagcaa aaccaagtgg 180
cttcttgtga agcactacag gtactaagcc cttcagccat atcacaccac tccccgtctg 240
attcaagctg acgcgtagcc gctgtctagt ccatactgcc accattgtat cagctacgcc 300
ccgaccttcc agacaaccta cgaattctac tacacatcca agccagaagg agctggcgac 360
acgagcttca ccgacttcta cgacttcaag tttgctgccg tgaactgtat cgcctacagc 420
gacctttgcg ttgagaatgg cgtcaagcta taccccacta cggttctata cgagaacggc 480
aaagaggtca aggccgtaac gggtggccag aacatcacct tcctttctga tctcatcgaa 540
gaagctttgg agaagtcgaa gcctggatct cggcccaagt ctctcgcatt gccccaaccg 600
ggcgacaaag agcgccccaa atctgagccc gagacagcat cgaggagcgc aaccgaggag 660
aagaagccca agaagccggt tgccacgccg aacgaagacg gagtgtcagt ttccttgacg 720
gccgaaaact tccagcgcct ggtgactatg actcaggatc cctggttcat caagttttac 780
gcgccgtggt gcccccattg ccaagacatg gcgcctacct gggagcagct ggcgaagaac 840
atgaagggca agctcaacat tggagaggtc aactgtgaca aggagtcgcg attgtgcaaa 900
gacgttggtg cgcgggcgtt tcccactatc ctgttcttca agggtggaga gcgctcagag 960
tacgaggggc tccgaggcct gggcgacttt atcaaatatg ccgaaaacgc cgtcgacctc 1020
gctagcggag tgcctgacgt ggacttggca gcattcaagg ctctcgagca gaaggaagac 1080
gtcatctttg tctactttta cgaccacgcc accacatcgg aggacttcaa tgccctcgag 1140
aggctgcccc tgagtctcat cggacatgcc aaactggtta agactaagga tccggccatg 1200
tacgagcgct tcaagatcac gacatggccc agattcatgg tttcgaggga gggtcgccct 1260
acgtactacc ctcccctcac ccctaacgcg atgagagata cccaccaagt tctggactgg 1320
atgaggtcgg tttggcttcc ccttgtcccc gaactgttgg ttaccaacgc ccgccagatc 1380
atggacaaca aaattgttgt gctcggcgtc ctgaatcgag aagaccagga atccttccag 1440
agtgctcttc gggagatgaa gagcgcagcc aacgagtgga tggacaggca aatccaagag 1500
ttccagttgg agcggaagaa gctgcgagac gcgaagcaaa tgaggatcga ggaagctgag 1560
gaccgagacg atgagcgcgc cctgcgggcc gccaaggcga tccatattga catgaacaat 1620
tccggacgga gagaagtggc ctttgcgtgg gttgatggcg tagcgtggca gcgctggatt 1680
cgaaccacgt atggcattga tgttaaggac ggagaaagag tcattatcaa cgaccaagat 1740
gtaagcctca agctcacccc catttgtcct ccctctacaa tattgctttg cgtttcgaac 1800
atgaacgact aacaaaaaca tttgaacaga gccgcaagta ctgggacagc accgtgacgg 1860
gcaactacat cctcgtcagc cgcacgtcca tcctggagac gctcgacaag gtcgtctaca 1920
ccccgcaggc cctcaagccc aagctcacca tttcctcttt cgagaagatc tttttcgaca 1980
tccgcgtctc cttcaccgag caccccctacc tgaccctggg ctgcatcgtt ggcatcgcct 2040
ttggagcctt ctcctggctg cgtggccgct ctcgccgtgg acgcggccac ttccggctcg 2100
aggattccat cagcattaga gatttcaagg acgggttcct tggtggatct aacggcaaca 2160

-continued ccaaggccga ctga 2174

<210> SEQ ID NO 7
<211> LENGTH: 1578
<212> TYPE: DNA
<213> ORGANISM: Trichoderma reesei

<400> SEQUENCE: 7
atgcatcagc aaaccctcct cgccaccctc gcggcgagtc tcgctgctct tccttttgct 60
caggcgggct tctattcgaa gagctctccc gtgctgcaag tagacgccaa gtcgtacgac 120
cgcctcatca caaagtcgaa tcatacctct gtaagtatcc gtcctcacac actcacctca 180
ctcacaacgc gacatcatat ctcatacaca tccaccccaa accaccacaa acacaagaca 240
tatatcaagc tcaaacacat acacatacat acaaacacat acacacacag atacatacac 300
aactctcata tatatgaacc attcattgac atttccccca agattgtcga attctacgcc 360
ccctggtgcg gccactgcca aaacctcaag cccgcctacg aaaaggccgc ccgcaccctc 420
gacggcctgg ccaaggtcgc cgccgtcgac tgcgacgacg acgccaacaa ggccctctgc 480
ggctccctcg gcgtcaaggg cttccccacc ctcaagatcg tccgccccgg caagaagccc 540
ggccgccccg tcgtcgagga ctaccagggc cagcgcaccg cgggcgccat tgccgacgcc 600
gtcgtcgcca agatcaacaa ccacgtcgtc aagctgacgg acaaggacat tgatgccttt 660
ctggaaaagg acggcgacaa gccaaaggcc atcttgttca cggaaaaggg aactacgagt 720
gcgctgctga ggagccttgc tattgatttt ctcgacgccg tgaccattgg ccaggtccgc 780
aacaaggaaa aggctgccgt cgacaggttc ggcatctctt cgttcccttc cttcgtcctc 840
atccccggag gcggcaagga gcccgtcgtc tacagcggcg agctcaacaa gaaggacatg 900
gtcgagttcc tcaagcaggt cgccgagccc aaccccgacc cggccccctc aaacggcaag 960
tccggcaaga aggcctccac caaggacaag gccagcagca aggaggcccc ccaaaaggcc 1020
gccgccgccg acgagtcttc gtccgccgca tcctccgaga cctcaacggc cgccgcgccg 1080
gagtcgaccc tcatcgacat ccccgccctg acttccaagg cagagctcga ggagcactgt 1140
ctccaaccaa agtcccaaac ctgcgtcctc gcctttgtgc ccgcgtccgc ctcggagatg 1200
cgcaacaaga tcctttctgc cgtctcccag ctgcacacca agtacgtcca cggaaagcgc 1260
cacttcccct tcttctctgt cgacagcgac gtcgaaggct ctgccgccct caaggaagcc 1320
ctcggcctct cgggcaagat tgagctcgtt gccctcaacg cccgccgggg gtggtggagg 1380
cgatacgagg acggtgagtt cagcgttcac agcgtcgagt cctggattga cgccgttcgc 1440
atgggcgagg gcgagaagaa gaagcttccc gagggagtcg tcgtcgagaa ggcggagccg 1500
gcggaggaag caaagtctga gactgaagct gccgcagctg atgaggccac tgagaagcct 1560
gagcacgatg agctctaa 1578

<210> SEQ ID NO 8
<211> LENGTH: 1167
<212> TYPE: DNA
<213> ORGANISM: Trichoderma reesei

<400> SEQUENCE: 8
atggtcttga tcaagagcct cgtgctcgcc gtcctggcca gctcggtggc tgccaagtcg 60
gccgtcatcg acctgattcc gtccaacttt gacaagcttg tcttctccgg aaagcccacg 120
cttgtcgagt tttttgctcc ctggtgcggc cactgcaaga accttgctcc cgtgtacgag 180
gagttggccc aggtgtttga gcatgctaag gacaaggtcc agattgcaaa ggtcgacgcc 240

-continued

```
gactcggagc gagacctcgg aaagcggttc ggcatccagg gcttccccac gctcaagttc    300

ttcgatggca agagcaagga gccgcaggag tacaagtcgg gccgtgatct ggacagcctg    360

accaagttca tcactgagaa gactggtgtc aagcccaaga agaagggcga gctgcccagc    420

agcgtggtga tgctgaacac taggaccttc cacgacactg ttggaggcga caagaatgtc    480

ctggtagcgt tcactgctcc ttggtgtggc cgtaagtgaa gcctcgaccc ccgactgagt    540

cttgattctc gcatatttac ctcttgacca gactgcaaga acctcgcccc cacttgggaa    600

aaggttgcca atgacttcgc gggtgatgag aacgttgtga ttgccaaggt cgatgccgag    660

ggcgctgaca gcaaggccgt cgccgaagag tacggcgtca ctggctaccc caccatcctc    720

ttcttccccg ctggcaccaa gaagcaggtt gactaccaag gcggccgatc ggagggtgac    780

tttgtcaact tcatcaacga gaaggccggc accttccgaa ccgagggcgg cgagctgaat    840

gacatcgccg gcaccgtggc gcccctcgac accatcgtgg ccaacttcct cagcggcacc    900

ggcttggccg aggctgctgc tgagatcaag gaggctgttg acctgcttac ggatgctgcg    960

gagaccaagt tcgccgagta ctacgtccgc gtcttcgaca agctgagcaa gaatgagaag   1020

tttgttaaca aggagcttgc gagactgcag ggcatcctgg ccaagggtgg ccttgcccct   1080

tctaagcggg atgagatcca gatcaagatc aacgtcctgc gcaaatttac ccccaaggag   1140

aacgaggacc agaaggacga gctgtga                                       1167
```

```
<210> SEQ ID NO 9
<211> LENGTH: 1705
<212> TYPE: DNA
<213> ORGANISM: Trichoderma reesei

<400> SEQUENCE: 9

atgcaacaga agcgtcttac tgctgccctg gtggccgctt tggccgctgt ggtctctgcc     60

gagtcggatg tcaagtcctt gaccaaggac accttcaacg acttcatcaa ctccaatgac    120

ctcgtcctgg ctgagtgtat gtctctctct ctctctctcc cccctcccc tttgccttct     180

gccctctcaa gcttctgcat ctctcgaccc ctcccccgcc agcccccgg catcgagatc     240

cccgctaaca gctgcaatct tccagtcttc gctccctggt gcggccactg caaggctctc    300

gcccccgagt acgaggaggc ggccacgact ctcaaggaca agagcatcaa gctcgccaag    360

gtcgactgtg tcgaggaggc tgacctctgc aaggagcatg gagttgaggg ctaccccacg    420

ctcaaggtct tccgtggcct cgataaggtc gctccctaca ctggtccccg caaggctgac    480

gggtaagctt tgaattgcac tgttctttgc atcaatccat tcattcgcta acgttggttg    540

tcctttcagc atcacctcct acatggtgaa gcagtccctg cctgccgtct ccgccctcac    600

caaggatacc ctcgaggact tcaagaccgc cgacaaggtc gtcctggtcg cctacatcgc    660

cgccgatgac aaggcctcca acgagacctt cactgctctg gccaacgagc tgcgtgacac    720

ctacctcttt ggtggcgtca acgatgctgc cgttgctgag gctgagggcg tcaagttccc    780

ttccattgtc ctctacaagt ccttcgacga gggcaagaac gtcttcagcg agaagttcga    840

tgctgaggcc attcgcaact ttgctcaggt tgccgccact cccctcgttg gcgaagttgg    900

ccctgagacc tacgccggct acatgtctgc cggtatccct ctggcttaca tcttcgccga    960

gaccgccgag gagcgtgaga acctggccaa gaccctcaag cccgtcgccg agaagtacaa   1020

gggcaagatc aacttcgcca ccatcgacgc caagaacttt ggctcgcacg ccggcaacat   1080

caacctcaag accgacaagt tccccgcctt tgccattcac gacattgaga agaacctcaa   1140

gttcccctt gaccagtcca aggagatcac cgagaaggac attgccgcct ttgtcgacgg    1200
```

-continued

```
cttctcctct ggcaagattg aggccagcat caagtccgag cccatccccg agacccagga   1260

gggccccgtc accgttgtcg ttgcccactc ttacaaggac attgtccttg acgacaagaa   1320

ggacgtcctg attgagttct acgctccctg gtgcggtcac tgcaaggctc tcgcccccaa   1380

gtacgatgag ctcgccagcc tgtatgccaa gagcgacttc aaggacaagg ttgtcatcgc   1440

caaggttgat gccactgcca acgacgtccc cgacgagatc cagggcttcc ccaccatcaa   1500

gctctacccc gccggtgaca agaagaaccc cgtcacctac agcggtgccc gcactgttga   1560

ggacttcatc gagttcatca aggagaacgg caagtacaag gccggcgtcg agatccccgc   1620

cgagcccacc gaggaggctg aggcttccga gtccaaggcc tctgaggagg ccaaggcttc   1680

cgaggagact cacgatgagc tgtaa                                         1705


<210> SEQ ID NO 10
<211> LENGTH: 982
<212> TYPE: DNA
<213> ORGANISM: Trichoderma reesei

<400> SEQUENCE: 10

atgaaggcag ccctgctcct ctccgccctg gcctcgtgcg ccattggcct cgtcgccgcc     60

gccgccgagg acttcaagat cgaggtcacc caccccgtcg agtgcgaccg caagacgcaa    120

aagggcgaca agctgtccat gcactaccgc ggcacgctgg ccaagacggg cgacaagttc    180

gatgccagtg cgtttcttct attccctttc cctctttcct cccatttctc tcacacacca    240

atgacggtcc tccttttctt ttgatctcat tgactgacaa gttttggtct acctactcta    300

ggctacgatc gtaaccagcc attcaacttc aagctgggtg ctggccaggt gattaagggg    360

ttcgtcttgc ccaccccccc ctaacccacc cctctcgttc ttttatgacg acgacgacga    420

cgacgacgtt gggcgacgtt gaggctaacg gcttgtagat gggatcaggg tctccttgac    480

atgtgcattg gcgagaagag gtaagacgaa ccgaaccaac ccaactgcgt cgctcactgc    540

ctccttgggc ctctatcagg acgcaatgct gaccattaca tcaccaattc aggactctca    600

cgatccctcc cgagctgggc tacggccagc gcaacatggg ccccattccc gccggctcaa    660

ccctgagtac gtggctccta tcctccccta cctgaactcc caaacccaga gtttcaccca    720

cgccgcatgg aaaaccaggc cgcaggctaa caacacacga tgccatacag tctttgagac    780

cgagctcctc gccatcgagg gcgtcaaggc cccccgagaag aagcccgtcc ccgagacgcc    840

cattgtcgag aagcccgccg aagagacaga ggagagcgtc gtcgagaagg ccgccgaggc    900

agccgccagc gtggcctccg aggccgtcga cgccgccaag actgtctttg ccgacactga    960

cgagggtcac ggggagctgt aa                                             982


<210> SEQ ID NO 11
<211> LENGTH: 809
<212> TYPE: DNA
<213> ORGANISM: Trichoderma  reesei

<400> SEQUENCE: 11

atgctgacct ttaggcggct cttcaccacc gccatcgtcc tggtggtggg cctgctcttc     60

ttcgtcaaga cggccgaggc cgccaagggc cccaagatca ccccacaaggt cttcttcgac    120

attgagcacg gcgacgagaa gctgggccgc atcgtcctgg gcctgtacgg caagacggtc    180

cccgagacgg ccgagaactt ccgggccctg gccaccggcg agaagggctt cggctacgag    240

ggctcgacct tccaccgcgt catcaagcag tttatgattc agggcggcga ctttaccaag    300

ggcgatggca ccggtggcaa gtcgagtaag ttgcctttgg ttcccaaata agcaatcaat    360
```

-continued

```
tgatcaatca attgggtggc atggcgtttg tcactgcatc tggctctggc tctggctaac    420

cttgagggct ccgtctagtc tacggcaaca agttcaagga cgagaacttc aagctgaagc    480

acaccaagaa gggcctgctg tccatggcca acgcgggacc cgacaccaac ggctcccagt    540

tcttcatcac cactgttgtt acctcgtatg atttccccac cctccttgga agatcctgga    600

taagaagtag gaccaatcta acgaacaact taaacagatg gctcgacggc cgacacgtcg    660

tcttcggcga ggttctcgag ggctacgaca ttgttgagaa gattgaaaac gtccagaccg    720

gccccggcga tcgcccagtg aagccggtca agattgccaa gagcggcgag ctggaggttc    780

cccccgaagg tattcacgtc gagctctaa                                      809
```

<210> SEQ ID NO 12
<211> LENGTH: 1372
<212> TYPE: DNA
<213> ORGANISM: Trichoderma reesei

<400> SEQUENCE: 12

```
atgatactgc gcgcggcaat cttcgtcttg ctggcgctgg tatcgctggc ggtttgcgcc     60

gaggactttt acaaggtatg ccgggacgca atgcctcgaa tcaagcacgg agcgtgctga    120

cggacacatg acaggttcta ggagtcgaca agtctgcgtc agacaagcag ctcaagcagg    180

cctatcgcca gctctccaag aagttccacc cagacaagaa cccgtacgcc ctcctacagc    240

tacacgcagt ctcgccaacc ttctccaatg tgctaatcac tctactgctt ctagaggcga    300

tgaaacggcg cacgagaaat tcgtgctggt gtccgaggcc tacgaagttc tgagcgattc    360

cgagcttcgc aaagtctacg accgctacgg ccacgagggc gtcaagtccc accgtcaagg    420

cggcggcgga ggaggaggag gcgacccctt cgacctcttc agcaggttct ttggcggcca    480

tggccacttt gggagaaaca gccgcgagcc ccggggcagc aacattgagg tccgcatcga    540

gatttccctc cgcgactttt acaacggcgc cacgaccgag ttccagtggg agaagcagca    600

catatgcgaa aagtgcgagg gcacgggcag cgcggacgga aaggtcgaga cgtgcagcgt    660

ctgcggcgga cacggggttc ggattgtcaa gcagcagctc gttcccggca tgttccagca    720

gatgcagatg cgctgcgacc actgtggcgg ctcgggcaag accatcaaga acaagtgttc    780

cgtctgccac ggcagccgag tcgagcgcaa gccgacgact gtcagcctga ctgtcgagag    840

gggcattgct cgagatgcca aggtggtgtt tgagaacgaa gccgaccaga gccccgactg    900

ggttcctggt gatctcattg tcaacctggg cgagaaggcc ccgtcatacg aagacaaccc    960

cgatcgcgtc gacggcacct tcttccggcg caagggccat gacctgtact ggaccgaggt   1020

tctgtcgctg cgtgaggcct ggatgggtgg ctggacgcgt aacctcacgc acctcgacaa   1080

gcacgttgtg cgtcttggac gggagcgagg ccaggttgtt cagagtgggt tggtggaaac   1140

cattcccggc gaaggcatgc ccatatggca cgaagaggga gagagcgtct atcacacaca   1200

cgagtttgga aatctctacg tcacatacga agtcattttg ccggaccaga tggacaagaa   1260

gatggagagc gagttctggg acctgtggga gaagtggcgg tccaagaatg gtgtggacct   1320

gcaaaaggat ctcgggcggc ctgagccagg gcatgaccat gatgagttat ga           1372
```

<210> SEQ ID NO 13
<211> LENGTH: 685
<212> TYPE: DNA
<213> ORGANISM: Trichoderma reesei

<400> SEQUENCE: 13

```
atggcgcgcc gccagcacct caccgcgaca gtcctgctgg ccgtcgtgct cttcttcagc     60
```

atcacgtacc tcctctcggg ctcgtccagc tccaatgcgg atcgaacgcg cgaggccgta 120
gtggcagagc ccaagtcgga attcaaggtg gattttgacg gcatgccggc caacctgctg 180
gagggagagt caatagcacc caagctggag aatgcgactc tcaagtacgt ttcccgcata 240
cccgaacctg ctcccatgag ccaccgacca tggcagtgtt tcaaaggata ccagttctga 300
cgcttttctg caattacata gagccgagct cggtcgcgca acatggaaat tcatgcacac 360
aatggtcgcc cgcttccccg agaagccctc gcccgaggag cgcaagacgc tcgagacctt 420
catctacctc ttcggccggc tgtacccctg cggcgactgc gcgaggcact tccggggcct 480
gctggcaaaa tatccgccgc agacgagtag ccggaatgcg gctgccggat ggctgtgttt 540
tgtgcacaac caggtcaacg agaggctgaa gaagcccata tttgactgca acaacattgg 600
cgacttttac gactgcggct gcggggacga gaagaaggac gggaaggagg aggccaaggt 660
tgatggcgaa ttggtgaagg aatag 685

<210> SEQ ID NO 14
<211> LENGTH: 3407
<212> TYPE: DNA
<213> ORGANISM: Trichoderma reesei

<400> SEQUENCE: 14
atggtgatgc tggtggcgat cgcgctcgca tggctgggat gctcgctgct gcggccggta 60
gatgccatgc gcgcagacta tctggcccag ctgcggcagg agacggtgga catgttctat 120
cacggatata gcaactacat ggagcatgcg tttcccgaag acgaggtggg ttccgctgcg 180
atagaagatt gttgttgggg ctgctgctat gttccagctc ccggggggtc ggattctctc 240
atatagaact agacagctaa cgacttgtgc cttttccata tgcttagctg cgtcccatat 300
cgtgcactcc cctgacgcga gatcgagaca atccggggcg catcagcctc aacgatgccc 360
tcggcaacta ctctctgacc ctcatagaca gcctgtctac ccttgccatc ctggccggcg 420
gcccgcagaa cggcccttac acgggaccgc aggctctgag cgacttccag gatggcgtgg 480
ccgagtttgt gcgacactac ggagacgggc gatcggggcc ctccggcgct gggatacgtg 540
ccagaggctt tgatctcgac agcaaagttc aggtctttga gaccgtcatc cggggcgtgg 600
gcggtctcct tagcgcgcac ctgttcgcca ttggggagct gccgattacc ggatacgtgc 660
ccaggccgga gggagtcgca ggcgatgatc ctctggagct ggcccctatt ccgtggccca 720
atgggttcag gtacgatggc cagctgctga ggctcgcgct cgacctctcc gagaggctgc 780
ttcccgcctt ctacacgccg acgggcattc cgtatcctcg tgtcaatctc cgcagcggca 840 tccccttta cgtcaactcg cctctccacc aaaacctggg cgaggcagtg gaggagcaga 900
gtggccgtcc tgaaattacc gagacctgca gcgccggggc gggaagcctg gttctcgaat 960
ttaccgtctt gagcaggctc acgggagacg ccaggtttga acaagccgcc aagcgagcat 1020
tctgggaggt ctggcatcgc aggagcgaaa ttggcttgat cgggaacggc atcgacgccg 1080
agcgcgggct gtggatcggc cctcacgcgg gcattggcgc gggcatggac agcttctttg 1140
aatatgcgct caagagccat atcctcctct cgggcctcgg tatgcccaac gcctccacgt 1200
cgcgccgaca gagcacaacc agctggctgg atccaaactc cctgcacccg ccgctgccac 1260
cagagatgca cacgtcagat gccttcctcc aggcatggca tcaggcgcac gcctcggtca 1320
agcggtacct gtacaccgac cggagccact tcccttatta ctccaacaac caccgtgcca 1380
cgggccagcc ctatgccatg tggatcgaca gcctgggcgc cttctatccg gggctcctcg 1440
ccctggccgg tgaggtggaa gaggccattg aggcgaacct cgtctacaca gccttgtgga 1500

-continued

```
cgcggtactc tgcgctgccc gaacgctggt ccgtccgcga aggcaacgtc gaggcaggca   1560

tcggctggtg gcccgggagg cccgagttca tcgagtcgac gtaccacatc taccgtgcaa   1620

cccgcgaccc gtggtatctg cacgttggcg agatggtcct ccgcgacatt cggcgtcggt   1680

gctatgcgga gtgcggctgg gccgggcttc aggacgtgca gacgggcgag aagcaggacc   1740

gcatggagag cttcttcttg ggagagacgg caaaatacat gtacctgctg ttcgacccag   1800

accatccact caacaagctg gatgccgcct acgtcttcac cacagaaggc catccgctta   1860

tcataccaaa gagcaaaagg ggtagcggct ctcacaacag acaggaccgc gctcgcaaag   1920

ccaagaagag ccgagacgtc gcagtctaca cctactacga tgaaagcttc acaaactctt   1980

gtccggcccc tcggccgcct tcagagcatc acctgatagg ctcggccacg gcggccaggc   2040

cagacttgtt ctccgtctct cgcttcacag acctgtacag aacgcccaac gtacacgggc   2100

ccctggagaa ggtggagatg cgagacaaga agaagggccg ggtggttcga tacagggcca   2160

cctcaaacca caccatcttc ccctggactc ttcccccagc catgctgccg gagaatggca   2220

cctgcgctgc tcccccggaa cgcatcatat ccttgattga gttcccggcc aacgacatca   2280

ccagtggaat cacgtcgcgg ttcggcaacc atctatcgtg gcagacgcat ctggggccaa   2340

cggtcaacat tctagaggga ctgaggctcc agctcgagca ggtgtcggac cctgccacgg   2400

gagaagacaa gtggaggatc acacacattg gcaacacgca gctggggcgc cacgagacag   2460

tcttcttcca cgcggaacac gtaaggcatc tcaaggacga ggtgttttcc tgccgcagaa   2520

ggagggacgc cgtggaaatc gagctcctgg tcgacaagcc gagcgatacc aacaacaaca   2580

acacgcttgc ctcgtccgat gacgatgtag tggtagatgc aaaagcagaa gagcaagacg   2640

gcatgctagc cgacgacgac ggcgacacac tcaacgcaga aacactctcc tccaactccc   2700

tcttccagtc cctcctccgc gccgtctcct ccgtcttcga gcccgtctac accgccatcc   2760

ccgagtccga ccccagcgcc ggcaccgcca aggtctacag tttcgacgcc tacacgtcca   2820

ccggccccgg cgcgtacccc atgccgtcca tctcggacac gcccatcccc ggcaacccct   2880

tttacaactt ccgcaacccg gcctccaact tcccctggtc gaccgtcttc ctcgccggcc   2940

aggcctgcga gggcccgctc cccgcgtccg cgccgcgcga gcaccaggtc attgtcatgc   3000

tccgcggcgg ctgctccttc agccgcaagc tggacaacat ccccagcttc tcgccccacg   3060

acagggcgct gcagctcgtc gttgtcctcg acgaaccgcc gccgccgccg ccgccgccgc   3120

cagccagtca gaacagcggc ggcgatgacg acgatgaaga tgacgaagac gaccacgacg   3180

ccgtcaacga caacgaagac gacaggcgcg acgtgacgcg gccactgctc gacacggagc   3240

agaccacgcc caagggcatg aagcgcctgc acggcatccc aatggtcctc gtccgagccg   3300

cgcggggcga ctacgagctt ttcgggcatg ccattggcgt gggcatgagg cgcaagtatc   3360

gggttgaaag ccaggggctt gtcgtggaga atgcggttgt gctgtga                 3407
```

<210> SEQ ID NO 15
<211> LENGTH: 1221
<212> TYPE: DNA
<213> ORGANISM: Trichoderma reesei

<400> SEQUENCE: 15

```
atgaggcctc tggcactcat atttgccctc atcttgggcc tattgctctg cttagcagcc     60

ccagcaacgg catcgtcatc atcatcacaa cactctcccc aagcggcatc agacgagtca    120

gatttaatat gtcacacatc aaacccagac gaatgctatc cccgggtctt cgtaccaacg    180

catgagttcc agccagtcca cgacgaccag caactcccaa acggcctcca tgtccgtctc    240
```

-continued

```
aacatctgga ccggccaaaa ggaagccaag atcaacgtcc ccgatgaggc caaccctgat    300

ctcgatggcc tgcccgtcga ccaagccgtg gttctcgtcg accaggagca gccagaaatt    360

atccagatcc ccaagggcgc accaaaatac gacaatgtcg gcaagatcaa ggaacccgcg    420

caagaaggag acgcccaaac ggaagccatt gcttttgcag agacgttcaa catgctcaag    480

accggcaagt cgccaagcgc cgaggagttc gacaacggac tggaaggcct ggaggagctc    540

tcccacgaca tctactacgg gctcaaaatc acagaggacg cggacgtggt caaggcgcta    600

ttctgcttga tgggggctcg cgacggcgac gcctcggagg gagccacgcc gcgcgaccag    660

caagcggccg cgatcctcgc cggcgccctg tccaacaatc cgtcggcact cgccgagata    720

gccaagatct ggcctgagct tctggactcg tcgtgtcctc gcgacggcgc caccatctct    780

gaccgtttct accaagacac cgtctccgtt gccgactctc cggcaaaggt caaggccgcc    840

gtctcggcca tcaacggcct gatcaaggac ggcgccatcc gaaagcagtt tctcgaaaac    900

agcggcatga agcagctcct ctcggtcctg tgccaagaga agccggagtg ggcgggagcg    960

cagcggaaag tcgctcagct ggtgctggac accttcctgg acgaggacat gggcgcccag   1020

cttggccagt ggcccagggg caaggcatcg aacaacgggg tgtgtgcggc gccggagacg   1080

gcgctcgatg acggatgctg ggactatcat gcggacagga tggtgaagct gcatgggacg   1140

ccgtggagca aggagttgaa gcagaggctg ggagatgcgc gcaaggcgaa cagcaagttg   1200

ccggatcatg gcgagctgta g                                              1221
```

<210> SEQ ID NO 16
<211> LENGTH: 664
<212> TYPE: PRT
<213> ORGANISM: Trichoderma reesei

<400> SEQUENCE: 16

```
Met Ala Arg Ser Arg Ser Ser Leu Ala Leu Gly Leu Gly Leu Leu Cys
1               5                   10                  15

Trp Ile Thr Leu Leu Phe Ala Pro Leu Ala Phe Val Gly Lys Ala Asn
            20                  25                  30

Ala Ala Ser Asp Asp Ala Asp Asn Tyr Gly Thr Val Ile Gly Ile Asp
        35                  40                  45

Leu Gly Thr Thr Tyr Ser Cys Val Gly Val Met Gln Lys Gly Lys Val
    50                  55                  60

Glu Ile Leu Val Asn Asp Gln Gly Asn Arg Ile Thr Pro Ser Tyr Val
65                  70                  75                  80

Ala Phe Thr Asp Glu Glu Arg Leu Val Gly Asp Ser Ala Lys Asn Gln
                85                  90                  95

Ala Ala Ala Asn Pro Thr Asn Thr Val Tyr Asp Val Lys Arg Leu Ile
            100                 105                 110

Gly Arg Lys Phe Asp Glu Lys Glu Ile Gln Ala Asp Ile Lys His Phe
        115                 120                 125

Pro Tyr Lys Val Ile Glu Lys Asn Gly Lys Pro Val Val Gln Val Gln
    130                 135                 140

Val Asn Gly Gln Lys Lys Gln Phe Thr Pro Glu Glu Ile Ser Ala Met
145                 150                 155                 160

Ile Leu Gly Lys Met Lys Glu Val Ala Glu Ser Tyr Leu Gly Lys Lys
                165                 170                 175

Val Thr His Ala Val Val Thr Val Pro Ala Tyr Phe Asn Asp Asn Gln
            180                 185                 190

Arg Gln Ala Thr Lys Asp Ala Gly Thr Ile Ala Gly Leu Asn Val Leu
        195                 200                 205
```

-continued

```
Arg Ile Val Asn Glu Pro Thr Ala Ala Ala Ile Ala Tyr Gly Leu Asp
    210                 215                 220

Lys Thr Asp Gly Glu Arg Gln Ile Ile Val Tyr Asp Leu Gly Gly Gly
225                 230                 235                 240

Thr Phe Asp Val Ser Leu Leu Ser Ile Asp Asn Gly Val Phe Glu Val
                245                 250                 255

Leu Ala Thr Ala Gly Asp Thr His Leu Gly Gly Glu Asp Phe Asp Gln
            260                 265                 270

Arg Ile Ile Asn Tyr Leu Ala Lys Ala Tyr Asn Lys Lys Asn Asn Val
        275                 280                 285

Asp Ile Ser Lys Asp Leu Lys Ala Met Gly Lys Leu Lys Arg Glu Ala
    290                 295                 300

Glu Lys Ala Lys Arg Thr Leu Ser Ser Gln Met Ser Thr Arg Ile Glu
305                 310                 315                 320

Ile Glu Ala Phe Phe Glu Gly Asn Asp Phe Ser Glu Thr Leu Thr Arg
                325                 330                 335

Ala Lys Phe Glu Glu Leu Asn Met Asp Leu Phe Lys Lys Thr Leu Lys
            340                 345                 350

Pro Val Glu Gln Val Leu Lys Asp Ala Asn Val Lys Lys Ser Glu Val
        355                 360                 365

Asp Asp Ile Val Leu Val Gly Gly Ser Thr Arg Ile Pro Lys Val Gln
    370                 375                 380

Ser Leu Ile Glu Glu Tyr Phe Asn Gly Lys Lys Ala Ser Lys Gly Ile
385                 390                 395                 400

Asn Pro Asp Glu Ala Val Ala Phe Gly Ala Ala Val Gln Ala Gly Val
                405                 410                 415

Leu Ser Gly Glu Glu Gly Thr Asp Asp Ile Val Leu Met Asp Val Asn
            420                 425                 430

Pro Leu Thr Leu Gly Ile Glu Thr Thr Gly Gly Val Met Thr Lys Leu
        435                 440                 445

Ile Pro Arg Asn Thr Pro Ile Pro Thr Arg Lys Ser Gln Ile Phe Ser
    450                 455                 460

Thr Ala Ala Asp Asn Gln Pro Val Val Leu Ile Gln Val Phe Glu Gly
465                 470                 475                 480

Glu Arg Ser Met Thr Lys Asp Asn Asn Leu Leu Gly Lys Phe Glu Leu
                485                 490                 495

Thr Gly Ile Pro Pro Ala Pro Arg Gly Val Pro Gln Ile Glu Val Ser
            500                 505                 510

Phe Glu Leu Asp Ala Asn Gly Ile Leu Lys Val Ser Ala His Asp Lys
        515                 520                 525

Gly Thr Gly Lys Gln Glu Ser Ile Thr Ile Thr Asn Asp Lys Gly Arg
    530                 535                 540

Leu Thr Gln Glu Glu Ile Asp Arg Met Val Ala Glu Ala Glu Lys Phe
545                 550                 555                 560

Ala Glu Glu Asp Lys Ala Thr Arg Glu Arg Ile Glu Ala Arg Asn Gly
                565                 570                 575

Leu Glu Asn Tyr Ala Phe Ser Leu Lys Asn Gln Val Asn Asp Glu Glu
            580                 585                 590

Gly Leu Gly Gly Lys Ile Asp Glu Glu Asp Lys Glu Thr Ile Leu Asp
        595                 600                 605

Ala Val Lys Glu Ala Thr Glu Trp Leu Glu Glu Asn Gly Ala Asp Ala
    610                 615                 620

Thr Thr Glu Asp Phe Glu Glu Gln Lys Glu Lys Leu Ser Asn Val Ala
```

-continued 625 630 635 640

Tyr Pro Ile Thr Ser Lys Met Tyr Gln Gly Ala Gly Gly Ser Glu Asp
645 650 655

Asp Gly Asp Phe His Asp Glu Leu
660

<210> SEQ ID NO 17
<211> LENGTH: 558
<212> TYPE: PRT
<213> ORGANISM: Trichoderma reesei

<400> SEQUENCE: 17

Met Lys Phe Asn Thr Val Ala Ala Ala Ala Ala Leu Leu Ala Gly Val
1 5 10 15

Ala Tyr Ala Glu Asp Val Glu Glu Ser Lys Ala Val Pro Glu Leu Pro
20 25 30

Thr Phe Thr Pro Thr Ser Ile Lys Ala Asp Phe Leu Glu Gln Phe Thr
35 40 45

Asp Asp Trp Glu Ser Arg Trp Lys Pro Ser His Ala Lys Lys Asp Thr
50 55 60

Ser Gly Ser Asp Lys Asp Ala Glu Glu Glu Trp Ala Tyr Val Gly Glu
65 70 75 80

Trp Ala Val Glu Glu Pro Tyr Gln Tyr Lys Gly Ile Asn Gly Asp Lys
85 90 95

Gly Leu Val Val Lys Asn Pro Ala Ala His His Ala Ile Ser Ala Lys
100 105 110

Phe Pro Lys Lys Ile Asp Asn Lys Gly Lys Thr Leu Val Val Gln Tyr
115 120 125

Glu Val Lys Leu Gln Lys Gly Leu Asp Cys Gly Gly Ala Tyr Met Lys
130 135 140

Leu Leu Arg Asp Asn Lys Ala Leu His Gln Asp Glu Phe Ser Asn Thr
145 150 155 160

Thr Pro Tyr Val Ile Met Phe Gly Pro Asp Lys Cys Gly His Asn Asn
165 170 175

Arg Val His Phe Ile Val Asn His Lys Asn Pro Lys Thr Gly Glu Tyr
180 185 190

Glu Glu Lys His Leu Asn Ser Ala Pro Ala Val Asn Ile Val Lys Thr
195 200 205

Thr Glu Leu Tyr Thr Leu Ile Val His Pro Asn Asn Thr Phe Ser Ile
210 215 220

Lys Gln Asn Gly Val Glu Thr Lys Ala Gly Ser Leu Leu Glu Asp Leu
225 230 235 240

Ser Pro Pro Ile Asn Pro Pro Lys Glu Ile Asp Asp Pro Lys Asp Ser
245 250 255

Lys Pro Asp Asp Trp Val Asp Glu Ala Arg Ile Pro Asp Pro Glu Ala
260 265 270

Val Lys Pro Glu Asp Trp Asp Glu Asp Ala Pro Phe Glu Ile Val Asp
275 280 285

Glu Glu Ala Val Lys Pro Glu Asp Trp Leu Glu Asp Glu Pro Thr Thr
290 295 300

Ile Pro Asp Pro Glu Ala Gln Lys Pro Glu Asp Trp Asp Asp Glu Glu
305 310 315 320

Asp Gly Asp Trp Ile Pro Pro Thr Val Pro Asn Pro Lys Cys Glu Asp
325 330 335

Val Ser Gly Cys Gly Pro Trp Thr Lys Pro Met Val Arg Asn Pro Asn

```
            340                 345                 350

Tyr Lys Gly Lys Trp Thr Ala Pro Tyr Ile Asp Asn Pro Ala Tyr Lys
        355                 360                 365

Gly Val Trp Ala Pro Arg Lys Ile Lys Asn Pro Asp Tyr Phe Glu Asp
    370                 375                 380

Lys Thr Pro Ala Asn Phe Glu Pro Met Gly Ala Ile Gly Phe Glu Ile
385                 390                 395                 400

Trp Thr Met Thr Asn Asp Ile Leu Phe Asp Asn Ile Tyr Ile Gly His
                405                 410                 415

Ser Ile Glu Asp Ala Glu Lys Leu Ala Asn Glu Thr Phe Phe Val Lys
            420                 425                 430

His Pro Ile Glu Lys Ala Leu Ala Glu Ala Asp Glu Pro Lys Phe Asp
        435                 440                 445

Asp Thr Pro Lys Ser Pro Ser Asp Leu Lys Phe Leu Asp Asp Pro Val
    450                 455                 460

Thr Phe Val Lys Glu Lys Leu Asp Leu Phe Leu Thr Ile Ala Gln Arg
465                 470                 475                 480

Asp Pro Val Glu Ala Ile Lys Phe Val Pro Glu Val Ala Gly Gly Ile
                485                 490                 495

Ala Ala Val Phe Val Thr Leu Ile Ala Ile Ile Val Gly Leu Val Gly
            500                 505                 510

Leu Gly Ser Ser Ser Ala Ala Pro Lys Lys Ala Ala Ala Thr Ala Lys
        515                 520                 525

Glu Lys Ala Lys Asp Val Ser Glu Ala Val Ala Ser Gly Ala Asp Lys
    530                 535                 540

Val Lys Gly Glu Val Thr Lys Arg Thr Thr Arg Ser Gln Ser
545                 550                 555


<210> SEQ ID NO 18
<211> LENGTH: 585
<212> TYPE: PRT
<213> ORGANISM: Trichoderma reesei

<400> SEQUENCE: 18

Met Lys Ser Ala Ser Lys Leu Phe Phe Leu Ser Val Phe Ser Leu Trp
1               5                   10                  15

Ala Thr Pro Gly Ala Cys Ser Ser Ser Ser Ser Thr Cys Thr Phe Ser
            20                  25                  30

Pro Asn Ala Ile Ile Asp Asp Gly Cys Val Ser Tyr Ala Thr Leu Asp
        35                  40                  45

Arg Leu Asn Val Lys Val Lys Pro Ala Ile Asp Glu Leu Val Gln Thr
    50                  55                  60

Thr Asp Phe Phe Ser His Tyr Arg Leu Asn Leu Phe Asn Lys Lys Cys
65                  70                  75                  80

Pro Phe Trp Asn Asp Glu Asp Gly Met Cys Gly Asn Ile Ala Cys Ala
                85                  90                  95

Val Glu Thr Leu Asp Asn Glu Glu Asp Ile Pro Glu Ile Trp Arg Ala
            100                 105                 110

His Glu Leu Ser Lys Leu Glu Gly Pro Arg Ala Lys His Pro Gly Lys
        115                 120                 125

Gln Glu Gln Arg Gln Asn Pro Glu Arg Pro Leu Gln Gly Glu Leu Gly
    130                 135                 140

Glu Asp Val Gly Glu Ser Cys Val Val Glu Tyr Asp Asp Glu Cys Asp
145                 150                 155                 160

Asp Arg Asp Tyr Cys Val Trp Asp Asp Glu Gly Ala Thr Ser Lys Gly
```

-continued

```
                165                 170                 175

Asp Tyr Ile Ser Leu Leu Arg Asn Pro Glu Arg Phe Thr Gly Tyr Gly
            180                 185                 190

Gly Gln Ser Ala Lys Gln Val Trp Asp Ala Ile Tyr Ser Glu Asn Cys
        195                 200                 205

Phe Lys Lys Ser Ser Phe Pro Lys Ser Ala Asp Leu Gly Val Ser His
    210                 215                 220

Arg Pro Thr Glu Ala Ala Ala Leu Asp Phe Lys Gln Val Leu Asp Thr
225                 230                 235                 240

Ala Gly Arg Gln Ala Gln Leu Glu Gln Gln Arg Gln Ser Asn Pro Asn
                245                 250                 255

Ile Pro Phe Val Ala Asn Thr Gly Tyr Glu Val Asp Asp Glu Cys Leu
            260                 265                 270

Glu Lys Arg Val Phe Tyr Arg Val Val Ser Gly Met His Ala Ser Ile
        275                 280                 285

Ser Val His Leu Cys Trp Asp Phe Leu Asn Gln Ser Thr Gly Gln Trp
    290                 295                 300

Gln Pro Asn Leu Asp Cys Tyr Glu Ser Arg Leu His Lys Phe Pro Asp
305                 310                 315                 320

Arg Ile Ser Asn Leu Tyr Phe Asn Tyr Ala Leu Val Thr Arg Ala Ile
                325                 330                 335

Ala Lys Leu Gly Pro Tyr Val Leu Ser Pro Gln Tyr Thr Phe Cys Thr
            340                 345                 350

Gly Asp Pro Leu Gln Asp Gln Glu Thr Arg Asp Lys Ile Ala Ala Val
        355                 360                 365

Thr Lys His Ala Ala Ser Val Pro Gln Ile Phe Asp Glu Gly Val Met
    370                 375                 380

Phe Val Asn Gly Glu Gly Pro Ser Leu Lys Glu Asp Phe Arg Asn Arg
385                 390                 395                 400

Phe Arg Asn Ile Ser Arg Val Met Asp Cys Val Gly Cys Asp Lys Cys
                405                 410                 415

Arg Leu Trp Gly Lys Ile Gln Thr Ser Gly Tyr Gly Thr Ala Leu Lys
            420                 425                 430

Ile Leu Phe Glu Phe Asn Glu Gly Gln Lys Pro Pro Pro Leu Lys Arg
        435                 440                 445

Thr Glu Leu Val Ala Leu Phe Asn Thr Tyr Ala Arg Leu Ser Ser Ser
    450                 455                 460

Val Ala Ala Val Gly Arg Phe Arg Ala Met Ile Asp Met Arg Asp Lys
465                 470                 475                 480

Met Ala Ser Lys Pro Asp Phe Lys Pro Glu Asp Leu Tyr Thr Leu Ile
                485                 490                 495

Asp Glu Ala Asp Glu Asp Met Asp Glu Phe Ile Arg Met Gln Asn Arg
            500                 505                 510

Gly Ser His Gly Asp Thr Leu Gly Glu Gln Val Gly Asn Glu Phe Ala
        515                 520                 525

Arg Val Met Met Ala Val Lys Ile Val Leu Lys Ser Trp Ile Arg Thr
    530                 535                 540

Pro Lys Met Ile Trp Gln Ile Val Ser Glu Glu Thr Ser Arg Leu Tyr
545                 550                 555                 560

Arg Ala Trp Val Gly Leu Pro Ala Arg Pro Arg Arg Tyr Ala Phe Arg
                565                 570                 575

Leu Pro Asn Leu Asn Arg Asp Glu Leu
            580                 585
```

-continued

<210> SEQ ID NO 19
<211> LENGTH: 1008
<212> TYPE: PRT
<213> ORGANISM: Trichoderma reesei

<400> SEQUENCE: 19

```
Met Lys Ser Pro Arg Lys Ser Pro Leu Leu Lys Leu Leu Gly Ala Ala
1               5                   10                  15

Phe Leu Phe Ser Thr Asn Val Leu Ala Ile Ser Ala Val Leu Gly Val
            20                  25                  30

Asp Leu Gly Thr Glu Tyr Ile Lys Ala Ala Leu Val Lys Pro Gly Ile
        35                  40                  45

Pro Leu Glu Ile Val Leu Thr Lys Asp Ser Arg Arg Lys Glu Thr Ser
    50                  55                  60

Ala Val Ala Phe Lys Pro Ala Lys Gly Ala Leu Pro Glu Gly Gln Tyr
65                  70                  75                  80

Pro Glu Arg Ser Tyr Gly Ala Asp Ala Met Ala Leu Ala Ala Arg Phe
                85                  90                  95

Pro Gly Glu Val Tyr Pro Asn Leu Lys Pro Leu Leu Gly Leu Pro Val
            100                 105                 110

Gly Asp Ala Ile Val Gln Glu Tyr Ala Ala Arg His Pro Ala Leu Lys
        115                 120                 125

Leu Gln Ala His Pro Thr Arg Gly Thr Ala Ala Phe Lys Thr Glu Thr
    130                 135                 140

Leu Ser Pro Glu Glu Glu Ala Trp Met Val Glu Glu Leu Leu Ala Met
145                 150                 155                 160

Glu Leu Gln Ser Ile Gln Lys Asn Ala Glu Val Thr Ala Gly Gly Asp
                165                 170                 175

Ser Ser Ile Arg Ser Ile Val Leu Thr Val Pro Pro Phe Tyr Thr Ile
            180                 185                 190

Glu Glu Lys Arg Ala Leu Gln Met Ala Ala Glu Leu Ala Gly Phe Lys
        195                 200                 205

Val Leu Ser Leu Val Ser Asp Gly Leu Ala Val Gly Leu Asn Tyr Ala
    210                 215                 220

Thr Ser Arg Gln Phe Pro Asn Ile Asn Glu Gly Ala Lys Pro Glu Tyr
225                 230                 235                 240

His Leu Val Phe Asp Met Gly Ala Gly Ser Thr Thr Ala Thr Val Met
                245                 250                 255

Arg Phe Gln Ser Arg Thr Val Lys Asp Val Gly Lys Phe Asn Lys Thr
            260                 265                 270

Val Gln Glu Ile Gln Val Leu Gly Ser Gly Trp Asp Arg Thr Leu Gly
        275                 280                 285

Gly Asp Ser Leu Asn Ser Leu Ile Ile Asp Asp Met Ile Ala Gln Phe
    290                 295                 300

Val Glu Ser Lys Gly Ala Gln Lys Ile Ser Ala Thr Ala Glu Gln Val
305                 310                 315                 320

Gln Ser His Gly Arg Ala Val Ala Lys Leu Ser Lys Glu Ala Glu Arg
                325                 330                 335

Leu Arg His Val Leu Ser Ala Asn Gln Asn Thr Gln Ala Ser Phe Glu
            340                 345                 350

Gly Leu Tyr Glu Asp Val Asp Phe Lys Tyr Lys Ile Ser Arg Ala Asp
        355                 360                 365

Phe Glu Thr Met Ala Lys Ala His Val Glu Arg Val Asn Ala Ala Ile
    370                 375                 380
```

```
Lys Asp Ala Leu Lys Ala Ala Asn Leu Glu Ile Gly Asp Leu Thr Ser
385                 390                 395                 400

Val Ile Leu His Gly Gly Ala Thr Arg Thr Pro Phe Val Arg Glu Ala
                405                 410                 415

Ile Glu Lys Ala Leu Gly Ser Gly Asp Lys Ile Arg Thr Asn Val Asn
            420                 425                 430

Ser Asp Glu Ala Ala Val Phe Gly Ala Ala Phe Arg Ala Ala Glu Leu
        435                 440                 445

Ser Pro Ser Phe Arg Val Lys Glu Ile Arg Ile Ser Glu Gly Ala Asn
    450                 455                 460

Tyr Ala Ala Gly Ile Thr Trp Lys Ala Ala Asn Gly Lys Val His Arg
465                 470                 475                 480

Gln Arg Leu Trp Thr Ala Pro Ser Pro Leu Gly Gly Pro Ala Lys Glu
                485                 490                 495

Ile Thr Phe Thr Glu Gln Glu Asp Phe Thr Gly Leu Phe Tyr Gln Gln
            500                 505                 510

Val Asp Thr Glu Asp Lys Pro Val Lys Ser Phe Ser Thr Lys Asn Leu
        515                 520                 525

Thr Ala Ser Val Ala Ala Leu Lys Glu Lys Tyr Pro Thr Cys Ala Asp
    530                 535                 540

Thr Gly Val Gln Phe Lys Ala Ala Ala Lys Leu Arg Thr Glu Asn Gly
545                 550                 555                 560

Glu Val Ala Ile Val Lys Ala Phe Val Glu Cys Glu Ala Glu Val Val
                565                 570                 575

Glu Lys Glu Gly Phe Val Asp Gly Val Lys Asn Leu Phe Gly Phe Gly
            580                 585                 590

Lys Lys Asp Gln Lys Pro Leu Ala Glu Gly Gly Asp Lys Asp Ser Ala
        595                 600                 605

Asp Ala Ser Ala Asp Ser Glu Ala Glu Thr Glu Glu Ala Ser Ser Ala
    610                 615                 620

Thr Lys Ser Ser Ser Ser Thr Ser Thr Thr Lys Ser Gly Asp Ala Ala
625                 630                 635                 640

Glu Ser Thr Glu Ala Ala Lys Glu Val Lys Lys Lys Gln Leu Val Ser
                645                 650                 655

Ile Pro Val Glu Val Thr Leu Glu Lys Ala Gly Ile Pro Gln Leu Thr
            660                 665                 670

Lys Ala Glu Trp Thr Lys Ala Lys Asp Arg Leu Lys Ala Phe Ala Ala
        675                 680                 685

Ser Asp Lys Ala Arg Leu Gln Arg Glu Glu Ala Leu Asn Gln Leu Glu
    690                 695                 700

Ala Phe Thr Tyr Lys Val Arg Asp Leu Val Asp Asn Glu Ala Phe Ile
705                 710                 715                 720

Ser Ala Ser Thr Glu Ala Glu Arg Gln Thr Leu Ser Glu Lys Ala Ser
                725                 730                 735

Glu Ala Ser Asp Trp Leu Tyr Glu Glu Gly Asp Ser Ala Thr Lys Asp
            740                 745                 750

Asp Phe Val Ala Lys Leu Lys Ala Leu Gln Asp Leu Val Ala Pro Ile
        755                 760                 765

Gln Asn Arg Leu Asp Glu Ala Glu Lys Arg Pro Gly Leu Ile Ser Asp
    770                 775                 780

Leu Arg Asn Ile Leu Asn Thr Thr Asn Val Phe Ile Asp Thr Val Arg
785                 790                 795                 800

Gly Gln Ile Ala Ala Tyr Asp Glu Trp Lys Ser Thr Ala Ser Ala Lys
                805                 810                 815
```

Ser Ala Glu Ser Ala Thr Ser Ser Ala Ala Ala Glu Ala Thr Thr Asn
820 825 830

Asp Phe Glu Gly Leu Glu Asp Glu Asp Asp Ser Pro Lys Glu Ala Glu
835 840 845

Glu Lys Pro Val Pro Glu Lys Val Val Pro Pro Leu His Asn Ser Glu
850 855 860

Glu Ile Asp Thr Leu Glu Val Leu Tyr Lys Glu Thr Leu Glu Trp Leu
865 870 875 880

Asn Lys Leu Glu Arg Gln Gln Ala Asp Val Pro Leu Thr Glu Glu Pro
885 890 895

Val Leu Val Val Ser Glu Leu Val Ala Arg Arg Asp Ala Leu Asp Lys
900 905 910

Ala Ser Leu Asp Leu Ala Leu Lys Ser Tyr Thr Gln Tyr Gln Lys Asn
915 920 925

Lys Pro Lys Lys Pro Thr Lys Ser Lys Lys Ala Lys Lys Gln Asp Lys
930 935 940

Thr Lys Ser Ala Asp Lys Ala Gly Pro Thr Phe Glu Phe Pro Glu Gly
945 950 955 960

Ser Val Pro Leu Ser Gly Glu Glu Leu Glu Glu Leu Val Lys Lys Tyr
965 970 975

Met Lys Glu Glu Glu Glu Thr Arg Arg Gln Ala Glu Gly Gly Gln Ala
980 985 990

Glu Glu Lys Pro Ala Glu Asp Thr Glu Lys Ser Ser His Asp Glu Leu
995 1000 1005

<210> SEQ ID NO 20
<211> LENGTH: 363
<212> TYPE: PRT
<213> ORGANISM: Trichoderma reesei

<400> SEQUENCE: 20

Met Val Ala Arg Leu Ser Ser Ile Tyr Ala Cys Gly Leu Leu Ala Trp
1 5 10 15

Thr His Ile Val Cys Ala Ser Gln Phe Ser Asp Pro Met Gln Leu Gln
20 25 30

Lys His Leu Ala Gln Asn Asp Tyr Thr Leu Ile Ala Phe Val Ala Ser
35 40 45

Arg Leu Glu Ala Asp Leu Lys Val Ser Leu Pro Leu Thr Ala Ser Thr
50 55 60

Ser Asn Gly Arg Glu Ala Ser Lys Leu Leu Leu Glu Glu Trp Gln Thr
65 70 75 80

Val Gln Gln His Val Ala Ser Thr Ala Thr Ile Asp Cys Pro Ser Ser
85 90 95

Pro Lys Leu Cys Gln Glu Met Asp Val Ala Ser Phe Pro Ala Ile Arg
100 105 110

Leu Tyr Arg Gln Asp Gly Ser Val Thr Arg Tyr Arg Gly Pro Arg Arg
115 120 125

Thr Ala Pro Ile Asp Ala Phe Val Lys Arg Ala Leu Lys Pro Ser Val
130 135 140

Gln Asn Val Pro Gly Gln Gln Leu Ala Asn Phe Ile Thr Asn Asp Asp
145 150 155 160

Tyr Val Phe Ile Ala Lys Leu Gln Gly Glu Ser Glu Ser Ile Asn Ser
165 170 175

His Tyr Arg Asp Phe Ala Gln Glu Tyr Ser Asp Arg Tyr Ser Phe Gly
180 185 190

```
Ile Ile Thr Ser Gly Ser Val Pro Ser Asn Gly Val Trp Cys Tyr Asn
        195                 200                 205

Asn Val Asp Gly Asn Gln His Ala Ala Thr Asp Leu Asn Asp Pro Asn
    210                 215                 220

Ala Leu Lys Lys Leu Leu Asn Leu Cys Thr Ala Glu Val Ile Pro Gln
225                 230                 235                 240

Leu Thr Arg Arg Asn Glu Met Thr Tyr Leu Ser Ser Gly Arg Ser Leu
                245                 250                 255

Val Tyr Tyr Phe Ser Asn Asn Glu Ala Asp Arg Glu Ala Tyr Val Lys
            260                 265                 270

Ala Leu Lys Pro Ile Ala Gln Arg Tyr Ala Glu Phe Leu Gln Phe Val
        275                 280                 285

Thr Val Asp Ser Gly Glu Tyr Pro Asp Met Leu Arg Asn Leu Gly Val
    290                 295                 300

Arg Ser Ala Gly Gly Leu Ala Val Gln Asn Val His Asn Gly His Ile
305                 310                 315                 320

Phe Pro Phe Arg Gly Asp Ala Ala Ala Ser Pro Gly Gln Val Asp Gln
                325                 330                 335

Phe Ile Val Ala Ile Ser Glu Gly Arg Ala Gln Pro Trp Asp Gly Arg
            340                 345                 350

Phe Asp Glu Gly Gln Glu Ala His Asp Glu Leu
        355                 360


<210> SEQ ID NO 21
<211> LENGTH: 688
<212> TYPE: PRT
<213> ORGANISM: Trichoderma reesei

<400> SEQUENCE: 21

Met Arg Leu Thr Ser Phe Phe Ser Gly Leu Ala Ala Phe Gly Leu Leu
1               5                   10                  15

Ser Ser Pro Ala Leu Ala Asp Asp Glu Ala Asp Asn Val Pro Ala Pro
            20                  25                  30

Thr Tyr Phe Asp Ser Val Met Val Pro Pro Leu Thr Glu Leu Thr Pro
        35                  40                  45

Asp Asn Phe Glu Lys Glu Ala Ser Lys Thr Lys Trp Leu Leu Val Lys
    50                  55                  60

His Tyr Ser Pro Tyr Cys His His Cys Ile Ser Tyr Ala Pro Thr Phe
65                  70                  75                  80

Gln Thr Thr Tyr Glu Phe Tyr Tyr Thr Ser Lys Pro Glu Gly Ala Gly
                85                  90                  95

Asp Thr Ser Phe Thr Asp Phe Tyr Asp Phe Lys Phe Ala Ala Val Asn
            100                 105                 110

Cys Ile Ala Tyr Ser Asp Leu Cys Val Glu Asn Gly Val Lys Leu Tyr
        115                 120                 125

Pro Thr Thr Val Leu Tyr Glu Asn Gly Lys Glu Val Lys Ala Val Thr
    130                 135                 140

Gly Gly Gln Asn Ile Thr Phe Leu Ser Asp Leu Ile Glu Glu Ala Leu
145                 150                 155                 160

Glu Lys Ser Lys Pro Gly Ser Arg Pro Lys Ser Leu Ala Leu Pro Gln
                165                 170                 175

Pro Gly Asp Lys Glu Arg Pro Lys Ser Glu Pro Glu Thr Ala Ser Arg
            180                 185                 190

Ser Ala Thr Glu Glu Lys Lys Pro Lys Lys Pro Val Ala Thr Pro Asn
        195                 200                 205
```

-continued

```
Glu Asp Gly Val Ser Val Ser Leu Thr Ala Glu Asn Phe Gln Arg Leu
    210                 215                 220

Val Thr Met Thr Gln Asp Pro Trp Phe Ile Lys Phe Tyr Ala Pro Trp
225                 230                 235                 240

Cys Pro His Cys Gln Asp Met Ala Pro Thr Trp Glu Gln Leu Ala Lys
                245                 250                 255

Asn Met Lys Gly Lys Leu Asn Ile Gly Glu Val Asn Cys Asp Lys Glu
            260                 265                 270

Ser Arg Leu Cys Lys Asp Val Gly Ala Arg Ala Phe Pro Thr Ile Leu
        275                 280                 285

Phe Phe Lys Gly Gly Glu Arg Ser Glu Tyr Glu Gly Leu Arg Gly Leu
    290                 295                 300

Gly Asp Phe Ile Lys Tyr Ala Glu Asn Ala Val Asp Leu Ala Ser Gly
305                 310                 315                 320

Val Pro Asp Val Asp Leu Ala Ala Phe Lys Ala Leu Glu Gln Lys Glu
                325                 330                 335

Asp Val Ile Phe Val Tyr Phe Tyr Asp His Ala Thr Thr Ser Glu Asp
            340                 345                 350

Phe Asn Ala Leu Glu Arg Leu Pro Leu Ser Leu Ile Gly His Ala Lys
        355                 360                 365

Leu Val Lys Thr Lys Asp Pro Ala Met Tyr Glu Arg Phe Lys Ile Thr
    370                 375                 380

Thr Trp Pro Arg Phe Met Val Ser Arg Glu Gly Arg Pro Thr Tyr Tyr
385                 390                 395                 400

Pro Pro Leu Thr Pro Asn Ala Met Arg Asp Thr His Gln Val Leu Asp
                405                 410                 415

Trp Met Arg Ser Val Trp Leu Pro Leu Val Pro Glu Leu Leu Val Thr
            420                 425                 430

Asn Ala Arg Gln Ile Met Asp Asn Lys Ile Val Val Leu Gly Val Leu
        435                 440                 445

Asn Arg Glu Asp Gln Glu Ser Phe Gln Ser Ala Leu Arg Glu Met Lys
    450                 455                 460

Ser Ala Ala Asn Glu Trp Met Asp Arg Gln Ile Gln Glu Phe Gln Leu
465                 470                 475                 480

Glu Arg Lys Lys Leu Arg Asp Ala Lys Gln Met Arg Ile Glu Glu Ala
                485                 490                 495

Glu Asp Arg Asp Asp Glu Arg Ala Leu Arg Ala Ala Lys Ala Ile His
            500                 505                 510

Ile Asp Met Asn Asn Ser Gly Arg Arg Glu Val Ala Phe Ala Trp Val
        515                 520                 525

Asp Gly Val Ala Trp Gln Arg Trp Ile Arg Thr Thr Tyr Gly Ile Asp
    530                 535                 540

Val Lys Asp Gly Glu Arg Val Ile Ile Asn Asp Gln Asp Val Ser Leu
545                 550                 555                 560

Lys Leu Thr Pro Ile Cys Pro Pro Ser Thr Ile Leu Leu Cys Ser Arg
                565                 570                 575

Lys Tyr Trp Asp Ser Thr Val Thr Gly Asn Tyr Ile Leu Val Ser Arg
            580                 585                 590

Thr Ser Ile Leu Glu Thr Leu Asp Lys Val Val Tyr Thr Pro Gln Ala
        595                 600                 605

Leu Lys Pro Lys Leu Thr Ile Ser Ser Phe Glu Lys Ile Phe Phe Asp
    610                 615                 620

Ile Arg Val Ser Phe Thr Glu His Pro Tyr Leu Thr Leu Gly Cys Ile
```

```
625                 630                 635                 640

Val Gly Ile Ala Phe Gly Ala Phe Ser Trp Leu Arg Gly Arg Ser Arg
                645                 650                 655

Arg Gly Arg Gly His Phe Arg Leu Glu Asp Ser Ile Ser Ile Arg Asp
            660                 665                 670

Phe Lys Asp Gly Phe Leu Gly Gly Ser Asn Gly Asn Thr Lys Ala Asp
        675                 680                 685


<210> SEQ ID NO 22
<211> LENGTH: 461
<212> TYPE: PRT
<213> ORGANISM: Trichoderma reesei

<400> SEQUENCE: 22

Met His Gln Gln Thr Leu Leu Ala Thr Leu Ala Ala Ser Leu Ala Ala
1               5                   10                  15

Leu Pro Phe Ala Gln Ala Gly Phe Tyr Ser Lys Ser Ser Pro Val Leu
            20                  25                  30

Gln Val Asp Ala Lys Ser Tyr Asp Arg Leu Ile Thr Lys Ser Asn His
        35                  40                  45

Thr Ser Ile Val Glu Phe Tyr Ala Pro Trp Cys Gly His Cys Gln Asn
    50                  55                  60

Leu Lys Pro Ala Tyr Glu Lys Ala Ala Arg Thr Leu Asp Gly Leu Ala
65                  70                  75                  80

Lys Val Ala Ala Val Asp Cys Asp Asp Asp Ala Asn Lys Ala Leu Cys
                85                  90                  95

Gly Ser Leu Gly Val Lys Gly Phe Pro Thr Leu Lys Ile Val Arg Pro
            100                 105                 110

Gly Lys Lys Pro Gly Arg Pro Val Val Glu Asp Tyr Gln Gly Gln Arg
        115                 120                 125

Thr Ala Gly Ala Ile Ala Asp Ala Val Val Ala Lys Ile Asn Asn His
    130                 135                 140

Val Val Lys Leu Thr Asp Lys Asp Ile Asp Ala Phe Leu Glu Lys Asp
145                 150                 155                 160

Gly Asp Lys Pro Lys Ala Ile Leu Phe Thr Glu Lys Gly Thr Thr Ser
                165                 170                 175

Ala Leu Leu Arg Ser Leu Ala Ile Asp Phe Leu Asp Ala Val Thr Ile
            180                 185                 190

Gly Gln Val Arg Asn Lys Glu Lys Ala Ala Val Asp Arg Phe Gly Ile
        195                 200                 205

Ser Ser Phe Pro Ser Phe Val Leu Ile Pro Gly Gly Gly Lys Glu Pro
    210                 215                 220

Val Val Tyr Ser Gly Glu Leu Asn Lys Lys Asp Met Val Glu Phe Leu
225                 230                 235                 240

Lys Gln Val Ala Glu Pro Asn Pro Asp Pro Ala Pro Ser Asn Gly Lys
                245                 250                 255

Ser Gly Lys Lys Ala Ser Thr Lys Asp Lys Ala Ser Ser Lys Glu Ala
            260                 265                 270

Pro Gln Lys Ala Ala Ala Ala Asp Glu Ser Ser Ser Ala Ala Ser Ser
        275                 280                 285

Glu Thr Ser Thr Ala Ala Ala Pro Glu Ser Thr Leu Ile Asp Ile Pro
    290                 295                 300

Ala Leu Thr Ser Lys Ala Glu Leu Glu Glu His Cys Leu Gln Pro Lys
305                 310                 315                 320

Ser Gln Thr Cys Val Leu Ala Phe Val Pro Ala Ser Ala Ser Glu Met
```

```
                325                 330                 335

Arg Asn Lys Ile Leu Ser Ala Val Ser Gln Leu His Thr Lys Tyr Val
            340                 345                 350

His Gly Lys Arg His Phe Pro Phe Phe Ser Val Asp Ser Asp Val Glu
        355                 360                 365

Gly Ser Ala Ala Leu Lys Glu Ala Leu Gly Leu Ser Gly Lys Ile Glu
    370                 375                 380

Leu Val Ala Leu Asn Ala Arg Arg Gly Trp Trp Arg Arg Tyr Glu Asp
385                 390                 395                 400

Gly Glu Phe Ser Val His Ser Val Glu Ser Trp Ile Asp Ala Val Arg
                405                 410                 415

Met Gly Glu Gly Glu Lys Lys Lys Leu Pro Glu Gly Val Val Val Glu
            420                 425                 430

Lys Ala Glu Pro Ala Glu Glu Ala Lys Ser Glu Thr Glu Ala Ala Ala
        435                 440                 445

Ala Asp Glu Ala Thr Glu Lys Pro Glu His Asp Glu Leu
    450                 455                 460


<210> SEQ ID NO 23
<211> LENGTH: 368
<212> TYPE: PRT
<213> ORGANISM: Trichoderma reesei

<400> SEQUENCE: 23

Met Val Leu Ile Lys Ser Leu Val Leu Ala Val Leu Ala Ser Ser Val
1               5                   10                  15

Ala Ala Lys Ser Ala Val Ile Asp Leu Ile Pro Ser Asn Phe Asp Lys
            20                  25                  30

Leu Val Phe Ser Gly Lys Pro Thr Leu Val Glu Phe Phe Ala Pro Trp
        35                  40                  45

Cys Gly His Cys Lys Asn Leu Ala Pro Val Tyr Glu Glu Leu Ala Gln
    50                  55                  60

Val Phe Glu His Ala Lys Asp Lys Val Gln Ile Ala Lys Val Asp Ala
65                  70                  75                  80

Asp Ser Glu Arg Asp Leu Gly Lys Arg Phe Gly Ile Gln Gly Phe Pro
                85                  90                  95

Thr Leu Lys Phe Phe Asp Gly Lys Ser Lys Glu Pro Gln Glu Tyr Lys
            100                 105                 110

Ser Gly Arg Asp Leu Asp Ser Leu Thr Lys Phe Ile Thr Glu Lys Thr
        115                 120                 125

Gly Val Lys Pro Lys Lys Lys Gly Glu Leu Pro Ser Ser Val Val Met
    130                 135                 140

Leu Asn Thr Arg Thr Phe His Asp Thr Val Gly Gly Asp Lys Asn Val
145                 150                 155                 160

Leu Val Ala Phe Thr Ala Pro Trp Cys Gly His Cys Lys Asn Leu Ala
                165                 170                 175

Pro Thr Trp Glu Lys Val Ala Asn Asp Phe Ala Gly Asp Glu Asn Val
            180                 185                 190

Val Ile Ala Lys Val Asp Ala Glu Gly Ala Asp Ser Lys Ala Val Ala
        195                 200                 205

Glu Glu Tyr Gly Val Thr Gly Tyr Pro Thr Ile Leu Phe Phe Pro Ala
    210                 215                 220

Gly Thr Lys Lys Gln Val Asp Tyr Gln Gly Gly Arg Ser Glu Gly Asp
225                 230                 235                 240

Phe Val Asn Phe Ile Asn Glu Lys Ala Gly Thr Phe Arg Thr Glu Gly
```

```
                245                 250                 255

Gly Glu Leu Asn Asp Ile Ala Gly Thr Val Ala Pro Leu Asp Thr Ile
            260                 265                 270

Val Ala Asn Phe Leu Ser Gly Thr Gly Leu Ala Glu Ala Ala Ala Glu
        275                 280                 285

Ile Lys Glu Ala Val Asp Leu Leu Thr Asp Ala Ala Glu Thr Lys Phe
    290                 295                 300

Ala Glu Tyr Tyr Val Arg Val Phe Asp Lys Leu Ser Lys Asn Glu Lys
305                 310                 315                 320

Phe Val Asn Lys Glu Leu Ala Arg Leu Gln Gly Ile Leu Ala Lys Gly
                325                 330                 335

Gly Leu Ala Pro Ser Lys Arg Asp Glu Ile Gln Ile Lys Ile Asn Val
            340                 345                 350

Leu Arg Lys Phe Thr Pro Lys Glu Asn Glu Asp Gln Lys Asp Glu Leu
        355                 360                 365


<210> SEQ ID NO 24
<211> LENGTH: 502
<212> TYPE: PRT
<213> ORGANISM: Trichoderma reesei

<400> SEQUENCE: 24

Met Gln Gln Lys Arg Leu Thr Ala Ala Leu Val Ala Ala Leu Ala Ala
1               5                   10                  15

Val Val Ser Ala Glu Ser Asp Val Lys Ser Leu Thr Lys Asp Thr Phe
            20                  25                  30

Asn Asp Phe Ile Asn Ser Asn Asp Leu Val Leu Ala Glu Phe Phe Ala
        35                  40                  45

Pro Trp Cys Gly His Cys Lys Ala Leu Ala Pro Glu Tyr Glu Glu Ala
    50                  55                  60

Ala Thr Thr Leu Lys Asp Lys Ser Ile Lys Leu Ala Lys Val Asp Cys
65                  70                  75                  80

Val Glu Glu Ala Asp Leu Cys Lys Glu His Gly Val Glu Gly Tyr Pro
                85                  90                  95

Thr Leu Lys Val Phe Arg Gly Leu Asp Lys Val Ala Pro Tyr Thr Gly
            100                 105                 110

Pro Arg Lys Ala Asp Gly Ile Thr Ser Tyr Met Val Lys Gln Ser Leu
        115                 120                 125

Pro Ala Val Ser Ala Leu Thr Lys Asp Thr Leu Glu Asp Phe Lys Thr
    130                 135                 140

Ala Asp Lys Val Val Leu Val Ala Tyr Ile Ala Ala Asp Asp Lys Ala
145                 150                 155                 160

Ser Asn Glu Thr Phe Thr Ala Leu Ala Asn Glu Leu Arg Asp Thr Tyr
                165                 170                 175

Leu Phe Gly Gly Val Asn Asp Ala Ala Val Ala Glu Ala Glu Gly Val
            180                 185                 190

Lys Phe Pro Ser Ile Val Leu Tyr Lys Ser Phe Asp Glu Gly Lys Asn
        195                 200                 205

Val Phe Ser Glu Lys Phe Asp Ala Glu Ala Ile Arg Asn Phe Ala Gln
    210                 215                 220

Val Ala Ala Thr Pro Leu Val Gly Glu Val Gly Pro Glu Thr Tyr Ala
225                 230                 235                 240

Gly Tyr Met Ser Ala Gly Ile Pro Leu Ala Tyr Ile Phe Ala Glu Thr
                245                 250                 255

Ala Glu Glu Arg Glu Asn Leu Ala Lys Thr Leu Lys Pro Val Ala Glu
```

```
            260                 265                 270

Lys Tyr Lys Gly Lys Ile Asn Phe Ala Thr Ile Asp Ala Lys Asn Phe
        275                 280                 285

Gly Ser His Ala Gly Asn Ile Asn Leu Lys Thr Asp Lys Phe Pro Ala
    290                 295                 300

Phe Ala Ile His Asp Ile Glu Lys Asn Leu Lys Phe Pro Phe Asp Gln
305                 310                 315                 320

Ser Lys Glu Ile Thr Glu Lys Asp Ile Ala Ala Phe Val Asp Gly Phe
                325                 330                 335

Ser Ser Gly Lys Ile Glu Ala Ser Ile Lys Ser Glu Pro Ile Pro Glu
            340                 345                 350

Thr Gln Glu Gly Pro Val Thr Val Val Val Ala His Ser Tyr Lys Asp
        355                 360                 365

Ile Val Leu Asp Asp Lys Lys Asp Val Leu Ile Glu Phe Tyr Ala Pro
    370                 375                 380

Trp Cys Gly His Cys Lys Ala Leu Ala Pro Lys Tyr Asp Glu Leu Ala
385                 390                 395                 400

Ser Leu Tyr Ala Lys Ser Asp Phe Lys Asp Lys Val Val Ile Ala Lys
                405                 410                 415

Val Asp Ala Thr Ala Asn Asp Val Pro Asp Glu Ile Gln Gly Phe Pro
            420                 425                 430

Thr Ile Lys Leu Tyr Pro Ala Gly Asp Lys Lys Asn Pro Val Thr Tyr
        435                 440                 445

Ser Gly Ala Arg Thr Val Glu Asp Phe Ile Glu Phe Ile Lys Glu Asn
    450                 455                 460

Gly Lys Tyr Lys Ala Gly Val Glu Ile Pro Ala Glu Pro Thr Glu Glu
465                 470                 475                 480

Ala Glu Ala Ser Glu Ser Lys Ala Ser Glu Glu Ala Lys Ala Ser Glu
                485                 490                 495

Glu Thr His Asp Glu Leu
            500


<210> SEQ ID NO 25
<211> LENGTH: 190
<212> TYPE: PRT
<213> ORGANISM: Trichoderma reesei

<400> SEQUENCE: 25

Met Lys Ala Ala Leu Leu Leu Ser Ala Leu Ala Ser Cys Ala Ile Gly
1               5                   10                  15

Leu Val Ala Ala Ala Ala Glu Asp Phe Lys Ile Glu Val Thr His Pro
            20                  25                  30

Val Glu Cys Asp Arg Lys Thr Gln Lys Gly Asp Lys Leu Ser Met His
        35                  40                  45

Tyr Arg Gly Thr Leu Ala Lys Thr Gly Asp Lys Phe Asp Ala Ser Tyr
    50                  55                  60

Asp Arg Asn Gln Pro Phe Asn Phe Lys Leu Gly Ala Gly Gln Val Ile
65                  70                  75                  80

Lys Gly Trp Asp Gln Gly Leu Leu Asp Met Cys Ile Gly Glu Lys Arg
                85                  90                  95

Thr Leu Thr Ile Pro Pro Glu Leu Gly Tyr Gly Gln Arg Asn Met Gly
            100                 105                 110

Pro Ile Pro Ala Gly Ser Thr Leu Ile Phe Glu Thr Glu Leu Leu Ala
        115                 120                 125

Ile Glu Gly Val Lys Ala Pro Glu Lys Lys Pro Val Pro Glu Thr Pro
```

```
    130                 135                 140

Ile Val Glu Lys Pro Ala Glu Glu Thr Glu Glu Ser Val Val Glu Lys
145                 150                 155                 160

Ala Ala Glu Ala Ala Ala Ser Val Ala Ser Glu Ala Val Asp Ala Ala
                165                 170                 175

Lys Thr Val Phe Ala Asp Thr Asp Glu Gly His Gly Glu Leu
            180                 185                 190


<210> SEQ ID NO 26
<211> LENGTH: 207
<212> TYPE: PRT
<213> ORGANISM: Trichoderma reesei

<400> SEQUENCE: 26

Met Leu Thr Phe Arg Arg Leu Phe Thr Thr Ala Ile Val Leu Val Val
1               5                   10                  15

Gly Leu Leu Phe Phe Val Lys Thr Ala Glu Ala Ala Lys Gly Pro Lys
            20                  25                  30

Ile Thr His Lys Val Phe Phe Asp Ile Glu His Gly Asp Glu Lys Leu
        35                  40                  45

Gly Arg Ile Val Leu Gly Leu Tyr Gly Lys Thr Val Pro Glu Thr Ala
    50                  55                  60

Glu Asn Phe Arg Ala Leu Ala Thr Gly Glu Lys Gly Phe Gly Tyr Glu
65                  70                  75                  80

Gly Ser Thr Phe His Arg Val Ile Lys Gln Phe Met Ile Gln Gly Gly
                85                  90                  95

Asp Phe Thr Lys Gly Asp Gly Thr Gly Gly Lys Ser Ile Tyr Gly Asn
            100                 105                 110

Lys Phe Lys Asp Glu Asn Phe Lys Leu Lys His Thr Lys Lys Gly Leu
        115                 120                 125

Leu Ser Met Ala Asn Ala Gly Pro Asp Thr Asn Gly Ser Gln Phe Phe
    130                 135                 140

Ile Thr Thr Val Val Thr Ser Trp Leu Asp Gly Arg His Val Val Phe
145                 150                 155                 160

Gly Glu Val Leu Glu Gly Tyr Asp Ile Val Glu Lys Ile Glu Asn Val
                165                 170                 175

Gln Thr Gly Pro Gly Asp Arg Pro Val Lys Pro Val Lys Ile Ala Lys
            180                 185                 190

Ser Gly Glu Leu Glu Val Pro Pro Glu Gly Ile His Val Glu Leu
        195                 200                 205


<210> SEQ ID NO 27
<211> LENGTH: 413
<212> TYPE: PRT
<213> ORGANISM: Trichoderma reesei

<400> SEQUENCE: 27

Met Ile Leu Arg Ala Ala Ile Phe Val Leu Leu Ala Leu Val Ser Leu
1               5                   10                  15

Ala Val Cys Ala Glu Asp Phe Tyr Lys Val Leu Gly Val Asp Lys Ser
            20                  25                  30

Ala Ser Asp Lys Gln Leu Lys Gln Ala Tyr Arg Gln Leu Ser Lys Lys
        35                  40                  45

Phe His Pro Asp Lys Asn Pro Gly Asp Glu Thr Ala His Glu Lys Phe
    50                  55                  60

Val Leu Val Ser Glu Ala Tyr Glu Val Leu Ser Asp Ser Glu Leu Arg
65                  70                  75                  80
```

-continued

Lys Val Tyr Asp Arg Tyr Gly His Glu Gly Val Lys Ser His Arg Gln
85 90 95

Gly Gly Gly Gly Gly Gly Gly Gly Asp Pro Phe Asp Leu Phe Ser Arg
100 105 110

Phe Phe Gly Gly His Gly His Phe Gly Arg Asn Ser Arg Glu Pro Arg
115 120 125

Gly Ser Asn Ile Glu Val Arg Ile Glu Ile Ser Leu Arg Asp Phe Tyr
130 135 140

Asn Gly Ala Thr Thr Glu Phe Gln Trp Glu Lys Gln His Ile Cys Glu
145 150 155 160

Lys Cys Glu Gly Thr Gly Ser Ala Asp Gly Lys Val Glu Thr Cys Ser
165 170 175

Val Cys Gly Gly His Gly Val Arg Ile Val Lys Gln Gln Leu Val Pro
180 185 190

Gly Met Phe Gln Gln Met Gln Met Arg Cys Asp His Cys Gly Gly Ser
195 200 205

Gly Lys Thr Ile Lys Asn Lys Cys Ser Val Cys His Gly Ser Arg Val
210 215 220

Glu Arg Lys Pro Thr Thr Val Ser Leu Thr Val Glu Arg Gly Ile Ala
225 230 235 240

Arg Asp Ala Lys Val Val Phe Glu Asn Glu Ala Asp Gln Ser Pro Asp
245 250 255

Trp Val Pro Gly Asp Leu Ile Val Asn Leu Gly Glu Lys Ala Pro Ser
260 265 270

Tyr Glu Asp Asn Pro Asp Arg Val Asp Gly Thr Phe Phe Arg Arg Lys
275 280 285

Gly His Asp Leu Tyr Trp Thr Glu Val Leu Ser Leu Arg Glu Ala Trp
290 295 300

Met Gly Gly Trp Thr Arg Asn Leu Thr His Leu Asp Lys His Val Val
305 310 315 320

Arg Leu Gly Arg Glu Arg Gly Gln Val Val Gln Ser Gly Leu Val Glu
325 330 335

Thr Ile Pro Gly Glu Gly Met Pro Ile Trp His Glu Glu Gly Glu Ser
340 345 350

Val Tyr His Thr His Glu Phe Gly Asn Leu Tyr Val Thr Tyr Glu Val
355 360 365

Ile Leu Pro Asp Gln Met Asp Lys Lys Met Glu Ser Glu Phe Trp Asp
370 375 380

Leu Trp Glu Lys Trp Arg Ser Lys Asn Gly Val Asp Leu Gln Lys Asp
385 390 395 400

Leu Gly Arg Pro Glu Pro Gly His Asp His Asp Glu Leu
405 410

<210> SEQ ID NO 28
<211> LENGTH: 182
<212> TYPE: PRT
<213> ORGANISM: Trichoderma reesei

<400> SEQUENCE: 28

Met Ala Arg Arg Gln His Leu Thr Ala Thr Val Leu Leu Ala Val Val
1 5 10 15

Leu Phe Phe Ser Ile Thr Tyr Leu Leu Ser Gly Ser Ser Ser Ser Asn
20 25 30

Ala Asp Arg Thr Arg Glu Ala Val Val Ala Glu Pro Lys Ser Glu Phe
35 40 45

Lys Val Asp Phe Asp Gly Met Pro Ala Asn Leu Leu Glu Gly Glu Ser
    50                  55                  60

Ile Ala Pro Lys Leu Glu Asn Ala Thr Leu Lys Ala Glu Leu Gly Arg
65                  70                  75                  80

Ala Thr Trp Lys Phe Met His Thr Met Val Ala Arg Phe Pro Glu Lys
                85                  90                  95

Pro Ser Pro Glu Glu Arg Lys Thr Leu Glu Thr Phe Ile Tyr Leu Phe
            100                 105                 110

Gly Arg Leu Tyr Pro Cys Gly Asp Cys Ala Arg His Phe Arg Gly Leu
        115                 120                 125

Leu Ala Lys Tyr Pro Pro Gln Thr Ser Ser Arg Asn Ala Ala Ala Gly
    130                 135                 140

Trp Leu Cys Phe Val His Asn Gln Val Asn Glu Arg Leu Lys Lys Pro
145                 150                 155                 160

Ile Phe Asp Cys Asn Asn Ile Gly Asp Phe Tyr Asp Cys Gly Cys Gly
                165                 170                 175

Asp Glu Lys Lys Asp Gly
            180

<210> SEQ ID NO 29
<211> LENGTH: 1070
<212> TYPE: PRT
<213> ORGANISM: Trichoderma reesei

<400> SEQUENCE: 29

Met Val Met Leu Val Ala Ile Ala Leu Ala Trp Leu Gly Cys Ser Leu
1               5                   10                  15

Leu Arg Pro Val Asp Ala Met Arg Ala Asp Tyr Leu Ala Gln Leu Arg
            20                  25                  30

Gln Glu Thr Val Asp Met Phe Tyr His Gly Tyr Ser Asn Tyr Met Glu
        35                  40                  45

His Ala Phe Pro Glu Asp Glu Leu Arg Pro Ile Ser Cys Thr Pro Leu
    50                  55                  60

Thr Arg Asp Arg Asp Asn Pro Gly Arg Ile Ser Leu Asn Asp Ala Leu
65                  70                  75                  80

Gly Asn Tyr Ser Leu Thr Leu Ile Asp Ser Leu Ser Thr Leu Ala Ile
                85                  90                  95

Leu Ala Gly Gly Pro Gln Asn Gly Pro Tyr Thr Gly Pro Gln Ala Leu
            100                 105                 110

Ser Asp Phe Gln Asp Gly Val Ala Glu Phe Val Arg His Tyr Gly Asp
        115                 120                 125

Gly Arg Ser Gly Pro Ser Gly Ala Gly Ile Arg Ala Arg Gly Phe Asp
    130                 135                 140

Leu Asp Ser Lys Val Gln Val Phe Glu Thr Val Ile Arg Gly Val Gly
145                 150                 155                 160

Gly Leu Leu Ser Ala His Leu Phe Ala Ile Gly Glu Leu Pro Ile Thr
                165                 170                 175

Gly Tyr Val Pro Arg Pro Glu Gly Val Ala Gly Asp Asp Pro Leu Glu
            180                 185                 190

Leu Ala Pro Ile Pro Trp Pro Asn Gly Phe Arg Tyr Asp Gly Gln Leu
        195                 200                 205

Leu Arg Leu Ala Leu Asp Leu Ser Glu Arg Leu Leu Pro Ala Phe Tyr
    210                 215                 220

Thr Pro Thr Gly Ile Pro Tyr Pro Arg Val Asn Leu Arg Ser Gly Ile
225                 230                 235                 240

-continued

```
Pro Phe Tyr Val Asn Ser Pro Leu His Gln Asn Leu Gly Glu Ala Val
                245                 250                 255

Glu Glu Gln Ser Gly Arg Pro Glu Ile Thr Glu Thr Cys Ser Ala Gly
            260                 265                 270

Ala Gly Ser Leu Val Leu Glu Phe Thr Val Leu Ser Arg Leu Thr Gly
        275                 280                 285

Asp Ala Arg Phe Glu Gln Ala Ala Lys Arg Ala Phe Trp Glu Val Trp
    290                 295                 300

His Arg Arg Ser Glu Ile Gly Leu Ile Gly Asn Gly Ile Asp Ala Glu
305                 310                 315                 320

Arg Gly Leu Trp Ile Gly Pro His Ala Gly Ile Gly Ala Gly Met Asp
                325                 330                 335

Ser Phe Phe Glu Tyr Ala Leu Lys Ser His Ile Leu Leu Ser Gly Leu
            340                 345                 350

Gly Met Pro Asn Ala Ser Thr Ser Arg Arg Gln Ser Thr Thr Ser Trp
        355                 360                 365

Leu Asp Pro Asn Ser Leu His Pro Pro Leu Pro Pro Glu Met His Thr
    370                 375                 380

Ser Asp Ala Phe Leu Gln Ala Trp His Gln Ala His Ala Ser Val Lys
385                 390                 395                 400

Arg Tyr Leu Tyr Thr Asp Arg Ser His Phe Pro Tyr Tyr Ser Asn Asn
                405                 410                 415

His Arg Ala Thr Gly Gln Pro Tyr Ala Met Trp Ile Asp Ser Leu Gly
            420                 425                 430

Ala Phe Tyr Pro Gly Leu Leu Ala Leu Ala Gly Glu Val Glu Glu Ala
        435                 440                 445

Ile Glu Ala Asn Leu Val Tyr Thr Ala Leu Trp Thr Arg Tyr Ser Ala
    450                 455                 460

Leu Pro Glu Arg Trp Ser Val Arg Glu Gly Asn Val Glu Ala Gly Ile
465                 470                 475                 480

Gly Trp Trp Pro Gly Arg Pro Glu Phe Ile Glu Ser Thr Tyr His Ile
                485                 490                 495

Tyr Arg Ala Thr Arg Asp Pro Trp Tyr Leu His Val Gly Glu Met Val
            500                 505                 510

Leu Arg Asp Ile Arg Arg Arg Cys Tyr Ala Glu Cys Gly Trp Ala Gly
        515                 520                 525

Leu Gln Asp Val Gln Thr Gly Glu Lys Gln Asp Arg Met Glu Ser Phe
    530                 535                 540

Phe Leu Gly Glu Thr Ala Lys Tyr Met Tyr Leu Leu Phe Asp Pro Asp
545                 550                 555                 560

His Pro Leu Asn Lys Leu Asp Ala Ala Tyr Val Phe Thr Thr Glu Gly
                565                 570                 575

His Pro Leu Ile Ile Pro Lys Ser Lys Arg Gly Ser Gly Ser His Asn
            580                 585                 590

Arg Gln Asp Arg Ala Arg Lys Ala Lys Lys Ser Arg Asp Val Ala Val
        595                 600                 605

Tyr Thr Tyr Tyr Asp Glu Ser Phe Thr Asn Ser Cys Pro Ala Pro Arg
    610                 615                 620

Pro Pro Ser Glu His His Leu Ile Gly Ser Ala Thr Ala Ala Arg Pro
625                 630                 635                 640

Asp Leu Phe Ser Val Ser Arg Phe Thr Asp Leu Tyr Arg Thr Pro Asn
                645                 650                 655

Val His Gly Pro Leu Glu Lys Val Glu Met Arg Asp Lys Lys Lys Gly
```

-continued

```
            660                 665                 670

Arg Val Val Arg Tyr Arg Ala Thr Ser Asn His Thr Ile Phe Pro Trp
        675                 680                 685

Thr Leu Pro Pro Ala Met Leu Pro Glu Asn Gly Thr Cys Ala Ala Pro
    690                 695                 700

Pro Glu Arg Ile Ile Ser Leu Ile Glu Phe Pro Ala Asn Asp Ile Thr
705                 710                 715                 720

Ser Gly Ile Thr Ser Arg Phe Gly Asn His Leu Ser Trp Gln Thr His
                725                 730                 735

Leu Gly Pro Thr Val Asn Ile Leu Glu Gly Leu Arg Leu Gln Leu Glu
            740                 745                 750

Gln Val Ser Asp Pro Ala Thr Gly Glu Asp Lys Trp Arg Ile Thr His
        755                 760                 765

Ile Gly Asn Thr Gln Leu Gly Arg His Glu Thr Val Phe Phe His Ala
    770                 775                 780

Glu His Val Arg His Leu Lys Asp Glu Val Phe Ser Cys Arg Arg Arg
785                 790                 795                 800

Arg Asp Ala Val Glu Ile Glu Leu Leu Val Asp Lys Pro Ser Asp Thr
                805                 810                 815

Asn Asn Asn Asn Thr Leu Ala Ser Ser Asp Asp Asp Val Val Val Asp
            820                 825                 830

Ala Lys Ala Glu Glu Gln Asp Gly Met Leu Ala Asp Asp Asp Gly Asp
        835                 840                 845

Thr Leu Asn Ala Glu Thr Leu Ser Ser Asn Ser Leu Phe Gln Ser Leu
    850                 855                 860

Leu Arg Ala Val Ser Ser Val Phe Glu Pro Val Tyr Thr Ala Ile Pro
865                 870                 875                 880

Glu Ser Asp Pro Ser Ala Gly Thr Ala Lys Val Tyr Ser Phe Asp Ala
                885                 890                 895

Tyr Thr Ser Thr Gly Pro Gly Ala Tyr Pro Met Pro Ser Ile Ser Asp
            900                 905                 910

Thr Pro Ile Pro Gly Asn Pro Phe Tyr Asn Phe Arg Asn Pro Ala Ser
        915                 920                 925

Asn Phe Pro Trp Ser Thr Val Phe Leu Ala Gly Gln Ala Cys Glu Gly
    930                 935                 940

Pro Leu Pro Ala Ser Ala Pro Arg Glu His Gln Val Ile Val Met Leu
945                 950                 955                 960

Arg Gly Gly Cys Ser Phe Ser Arg Lys Leu Asp Asn Ile Pro Ser Phe
                965                 970                 975

Ser Pro His Asp Arg Ala Leu Gln Leu Val Val Val Leu Asp Glu Pro
            980                 985                 990

Pro Pro Pro Pro Pro Pro Pro Pro  Ala Asn Asp Arg Arg  Asp Val Thr
        995                 1000                1005

Arg Pro  Leu Leu Asp Thr Glu  Gln Thr Thr Pro Lys  Gly Met Lys
    1010                1015                1020

Arg Leu  His Gly Ile Pro Met  Val Leu Val Arg Ala  Ala Arg Gly
    1025                1030                1035

Asp Tyr  Glu Leu Phe Gly His  Ala Ile Gly Val Gly  Met Arg Arg
    1040                1045                1050

Lys Tyr  Arg Val Glu Ser Gln  Gly Leu Val Val Glu  Asn Ala Val
    1055                1060                1065

Val Leu
    1070
```

<210> SEQ ID NO 30
<211> LENGTH: 406
<212> TYPE: PRT
<213> ORGANISM: Trichoderma reesei

<400> SEQUENCE: 30

```
Met Arg Pro Leu Ala Leu Ile Phe Ala Leu Ile Leu Gly Leu Leu Leu
1               5                   10                  15

Cys Leu Ala Ala Pro Ala Thr Ala Ser Ser Ser Ser Ser Gln His Ser
            20                  25                  30

Pro Gln Ala Ala Ser Asp Glu Ser Asp Leu Ile Cys His Thr Ser Asn
        35                  40                  45

Pro Asp Glu Cys Tyr Pro Arg Val Phe Val Pro Thr His Glu Phe Gln
    50                  55                  60

Pro Val His Asp Asp Gln Gln Leu Pro Asn Gly Leu His Val Arg Leu
65                  70                  75                  80

Asn Ile Trp Thr Gly Gln Lys Glu Ala Lys Ile Asn Val Pro Asp Glu
                85                  90                  95

Ala Asn Pro Asp Leu Asp Gly Leu Pro Val Asp Gln Ala Val Val Leu
            100                 105                 110

Val Asp Gln Glu Gln Pro Glu Ile Ile Gln Ile Pro Lys Gly Ala Pro
        115                 120                 125

Lys Tyr Asp Asn Val Gly Lys Ile Lys Glu Pro Ala Gln Glu Gly Asp
    130                 135                 140

Ala Gln Thr Glu Ala Ile Ala Phe Ala Glu Thr Phe Asn Met Leu Lys
145                 150                 155                 160

Thr Gly Lys Ser Pro Ser Ala Glu Glu Phe Asp Asn Gly Leu Glu Gly
                165                 170                 175

Leu Glu Glu Leu Ser His Asp Ile Tyr Tyr Gly Leu Lys Ile Thr Glu
            180                 185                 190

Asp Ala Asp Val Val Lys Ala Leu Phe Cys Leu Met Gly Ala Arg Asp
        195                 200                 205

Gly Asp Ala Ser Glu Gly Ala Thr Pro Arg Asp Gln Gln Ala Ala Ala
    210                 215                 220

Ile Leu Ala Gly Ala Leu Ser Asn Asn Pro Ser Ala Leu Ala Glu Ile
225                 230                 235                 240

Ala Lys Ile Trp Pro Glu Leu Leu Asp Ser Ser Cys Pro Arg Asp Gly
                245                 250                 255

Ala Thr Ile Ser Asp Arg Phe Tyr Gln Asp Thr Val Ser Val Ala Asp
            260                 265                 270

Ser Pro Ala Lys Val Lys Ala Ala Val Ser Ala Ile Asn Gly Leu Ile
        275                 280                 285

Lys Asp Gly Ala Ile Arg Lys Gln Phe Leu Glu Asn Ser Gly Met Lys
    290                 295                 300

Gln Leu Leu Ser Val Leu Cys Gln Glu Lys Pro Glu Trp Ala Gly Ala
305                 310                 315                 320

Gln Arg Lys Val Ala Gln Leu Val Leu Asp Thr Phe Leu Asp Glu Asp
                325                 330                 335

Met Gly Ala Gln Leu Gly Gln Trp Pro Arg Gly Lys Ala Ser Asn Asn
            340                 345                 350

Gly Val Cys Ala Ala Pro Glu Thr Ala Leu Asp Asp Gly Cys Trp Asp
        355                 360                 365

Tyr His Ala Asp Arg Met Val Lys Leu His Gly Thr Pro Trp Ser Lys
    370                 375                 380
```

```
Glu Leu Lys Gln Arg Leu Gly Asp Ala Arg Lys Ala Asn Ser Lys Leu
385                 390                 395                 400

Pro Asp His Gly Glu Leu
                405


<210> SEQ ID NO 31
<211> LENGTH: 51
<212> TYPE: DNA
<213> ORGANISM: Artificial Sequence
<220> FEATURE:
<223> OTHER INFORMATION: F-attB1 PCR primer

<400> SEQUENCE: 31

ggggacaagt ttgtacaaaa aagcaggcta tggctcgttc acggagctcc c              51


<210> SEQ ID NO 32
<211> LENGTH: 53
<212> TYPE: DNA
<213> ORGANISM: Artificial Sequence
<220> FEATURE:
<223> OTHER INFORMATION: R-attB2 PCR primer

<400> SEQUENCE: 32

ggggaccact ttgtacaaga aagctgggtt tacaattcgt cgtggaagtc gcc            53


<210> SEQ ID NO 33
<211> LENGTH: 21
<212> TYPE: DNA
<213> ORGANISM: Trichoderma reesei

<400> SEQUENCE: 33

agttaccacg agcggtaaca g                                               21


<210> SEQ ID NO 34
<211> LENGTH: 20
<212> TYPE: DNA
<213> ORGANISM: Trichoderma reesei

<400> SEQUENCE: 34

aagagaactc gttgccaagc                                                 20


<210> SEQ ID NO 35
<211> LENGTH: 20
<212> TYPE: DNA
<213> ORGANISM: Trichoderma reesei

<400> SEQUENCE: 35

caccaacacc gtctacgatg                                                 20


<210> SEQ ID NO 36
<211> LENGTH: 23
<212> TYPE: DNA
<213> ORGANISM: Trichoderma reesei

<400> SEQUENCE: 36

cgttcttctc aatgaccttg tag                                             23


<210> SEQ ID NO 37
<211> LENGTH: 16
<212> TYPE: DNA
<213> ORGANISM: Bos taurus

<400> SEQUENCE: 37

cagcaagctc gtcggc                                                     16
```

<210> SEQ ID NO 38
<211> LENGTH: 22
<212> TYPE: DNA
<213> ORGANISM: Bos taurus

<400> SEQUENCE: 38
ggtacatctt gccgttgatc tc 22

<210> SEQ ID NO 39
<211> LENGTH: 12
<212> TYPE: DNA
<213> ORGANISM: Artificial Sequence
<220> FEATURE:
<223> OTHER INFORMATION: CBHI linker region with SpeI restriction site change

<400> SEQUENCE: 39
actagtaccc ag 12

<210> SEQ ID NO 40
<211> LENGTH: 23
<212> TYPE: DNA
<213> ORGANISM: Artificial Sequence
<220> FEATURE:
<223> OTHER INFORMATION: hph1 PCR primer

<400> SEQUENCE: 40
tctccggtgt cccttgtccc ttc 23

<210> SEQ ID NO 41
<211> LENGTH: 23
<212> TYPE: DNA
<213> ORGANISM: Artificial Sequence
<220> FEATURE:
<223> OTHER INFORMATION: hph2 PCR primer

<400> SEQUENCE: 41
acctgtggcg ccggtgatgc cgg 23

<210> SEQ ID NO 42
<211> LENGTH: 1113
<212> TYPE: DNA
<213> ORGANISM: Artificial Sequence
<220> FEATURE:
<223> OTHER INFORMATION: Synthetic prochymosin gene

<400> SEQUENCE: 42
actagtgccg agatcacccg catccctctc tacaagggca agagcctccg caaggccctc 60
aaggagcacg gcctcctcga ggacttcctc cagaagcagc agtacggcat cagcagcaag 120
tacagcggct tcggcgaggt cgccagcgtc cctctcacca actacctcga cagccagtac 180
ttcggcaaga tctacctcgg cacccctcct caggagttca ccgtcctctt cgacaccggc 240
agcagcgact tctgggtccc gagcatctac tgcaagagca acgcctgcaa gaaccaccag 300
cgcttcgacc ctcgcaagag cagcaccttc cagaacctcg gcaagcctct cagcatccac 360
tacggcaccg gcagcatgca gggcatcctc ggctacgaca ccgtcacggt ctccaacatc 420
gtcgacatcc agcagactgt cggcctcagc acccaggagc ctggcgacgt ctttacctac 480
gccgagttcg acggcatcct gggcatggcc taccctagcc tcgccagcga gtacagcatc 540
cctgtctttg acaacatgat gaaccgccac ctcgtcgccc aggacctctt cagcgtctac 600
atggaccgca acggccaaga gagcatgctc accctcggcg ccatcgaccc tagctactac 660
accggcagcc tccactgggt cccggtcacc gtccagcagt actggcagtt caccgtcgac 720

-continued

```
agcgtcacca tcagcggcgt cgtcgtcgcc tgcgagggcg gctgccaggc catcctggac    780

accggcacca gcaagctcgt cggccctagc agcgacatcc tgaacatcca gcaggccatc    840

ggcgccaccc agaaccagta cggcgagttc gacatcgact gcgacaacct cagctacatg    900

cctaccgtcg tctttgagat caacggcaag atgtaccctc tcacccctag cgcctacacc    960

agccaggacc agggcttctg caccagcggc ttccagagcg agaaccacag ccagaagtgg   1020

atcctcggcg acgtctttat ccgcgagtac tacagcgtct ttgaccgcgc caacaacctc   1080

gtcggcctcg ccaaggccat ctaaggcgcg ccg                                1113
```

OVER EXPRESSION OF FOLDASES AND CHAPERONES IMPROVES PROTEIN PRODUCTION

This application claims priority of U.S. Provisional applications 60/919,332, filed Mar. 21, 2007, the contents of which is herein incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "30969US_SequenceListing.txt", created on Jan. 15, 2013, which is 104943 bytes in size.

INTRODUCTION

Protein secretion is an important aspect of protein production in various cell expression systems. One of the factors associated with protein secretion is protein folding. Many proteins can be reversibly unfolded and refolded in vitro at dilute concentrations since all of the information required to specify a compact folded protein structure is present in the amino acid sequence of a protein. However, protein folding in vivo occurs in a concentrated milieu of numerous proteins in which intermolecular aggregation reactions compete with the intramolecular folding process. The first step in the eukaryotic secretory pathway is translocation of the nascent polypeptide across the ER membrane in extended form. Correct folding and assembly of a polypeptide occurs in the ER through the secretory pathway. Many proteins are often highly overexpressed, but poorly secreted even though secretion signals are present on these proteins. There is a need in the art to produce proteins efficiently in cellular production systems.

SUMMARY

The present teachings are based, at least in part, on the discovery that protein secretion in filamentous fungi can be modulated by a group of chaperones and/or foldases. Accordingly the present teachings provide methods for increasing protein secretion in filamentous fungi by co-expressing certain chaperone(s) and/or foldase(s). The present teachings also provide filamentous fungi containing certain chaperone(s) and/or foldase(s) and a protein of interest for increased secretion.

In some embodiments, the present teachings provide a method for increasing the secretion of a secretable polypeptide in a filamentous fungus host. The method comprises expressing a secretion enhancing protein in a filamentous fungus host containing a secretable polypeptide, wherein the secretion enhancing protein comprises bip1, clx1, ero1, lhs1, prp3, prp4, prp1, tig1, pdi1, ppi1, ppi2, Scj1, erv2, EDEM, and/or sil1, and wherein the secretable polypeptide can be a chymosin.

In some embodiments, the present teachings provide a filamentous fungus host containing a first polynucleotide encoding a secretion enhancing protein and a second polynucleotide encoding a chymosin, wherein the secretion enhancing protein comprises bip1, clx1, ero1, lhs1, prp3, prp4, prp1, tig1, pdi1, ppi1, ppi2, Scj1, erv2, EDEM, and/or sil1, and wherein the first polynucleotide can be operably linked to a first promoter and the second polynucleotide can be operably linked to a second promoter.

One aspect of the invention is a method for production of a secretable polypeptide in a filamentous fungal host by expressing a secretion enhancing protein in a filamentous fungal host containing a secretable polypeptide, wherein the secretion enhancing protein is bip1 and the secretable polypeptide is a chymosin. In some embodiments, at least two secretion enhancing proteins are expressed. In some embodiments, the method includes expression of at least a second chaperone protein and/or a foldase. In some embodiments, the filamentous fungal host is *T. reesei*. In some embodiments, the host is selected from the following hosts: *Aspergillus, Acremonium, Aureobasidium, Beauveria, Cephalosporium, Ceriporiopsis, Chaetomium paecilomyces, Chrysosporium, Claviceps, Cochiobolus, Cryptococcus, Cyathus, Endothia, Endothia mucor, Fusarium, Gilocladium, Humicola, Magnaporthe, Myceliophthora, Myrothecium, Mucor, Neurospora, Phanerochaete, Podospora, Paecilomyces, Penicillium, Pyricularia, Rhizomucor, Rhizopus, Schizophylum, Stagonospora, Talaromyces, Trichoderma, Thermomyces, Thermoascus, Thielavia, Tolypocladium, Trichophyton, Trametes*, and *Pleurotus*. In some embodiments, the chymosin is a bovine chymosin. In some embodiments, the chymosin is expressed through a promoter of the filamentous fungal host. In further embodiments, the chymosin is expressed under a cbh1 promoter in *T. reesei*. In some embodiments, the chymosin is produced as a fusion protein. In some embodiments, the chymosin is produced as a fusion protein with a CBHI, or a portion thereof. In some embodiments, the chymosin is produced as a fusion protein with a CBHI, or a portion thereof, and the CBHI amino acid sequence is altered to reduce or eliminate catalytic activity. In other embodiments, the method includes inoculating a suitable growth medium with the host and incubating under conditions permitting growth of the host.

Other aspects of the invention include a filamentous fungal host having a first polynucleotide encoding a secretion enhancing protein and a second polynucleotide encoding a chymosin, wherein the secretion enhancing protein is bip1, and wherein the first polynucleotide is operably linked to a first promoter and the second polynucleotide is operably linked to a second promoter. In some embodiments, the host also contains a third polynucleotide operably linked to a third promoter, wherein the third polynucleotide encodes a secretion enhancing protein selected from: bip1, clx1, ero1, lhs1, prp3, prp4, prp1, tig1, pdi1, ppi1, ppi2, Scj1, erv2, EDEM, and sil1. In some embodiments, the first polynucleotide encodes a chaperone protein and the third polynucleotide encodes a foldase. In some embodiments, the first promoter and the third promoter is a constitutive promoter. In some embodiments, the first promoter is a constitutive promoter. In some embodiments, the filamentous fungus is *T. reesei*. In some embodiments, the second promoter is a promoter obtained from the filamentous fungal host. In some embodiments, the filamentous fungus is *T. reesei* and the second promoter is a CBH1 promoter of *T. reesei*. In some embodiments, the second polynucleotide encodes a bovine chymosin. In some embodiments, the secretion level of the chymosin in the filamentous fungus is at least 50 mg/liter when the filamentous fungus grows in a fermentation condition.

Further aspects of the invention include a biologically pure culture comprising a population of filamentous fungi disclosed above. In some embodiments, the culture also contains the chymosin secreted by the filamentous fungi.

Further aspects of the invention include a supernatant obtained from a culture of the filamentous fungus host, wherein the supernatant contains substantial amount of chymosin, but not substantial amount of the filamentous fungus.

Further aspects of the invention include a supernatant obtained using the method disclosed above, wherein the supernatant contains substantial amount of chymosin, but not substantial amount of the filamentous fungus.

BRIEF DESCRIPTION OF THE DRAWINGS

The skilled artisan will understand that the drawings are for illustration purposes only. The drawings are not intended to limit the scope of the present teaching in any way.

FIG. 2 is the DNA sequence of a synthetic prochymosin gene (SEQ ID NO: 42).

DESCRIPTION OF VARIOUS EMBODIMENTS

Definition Section

Figure 1:
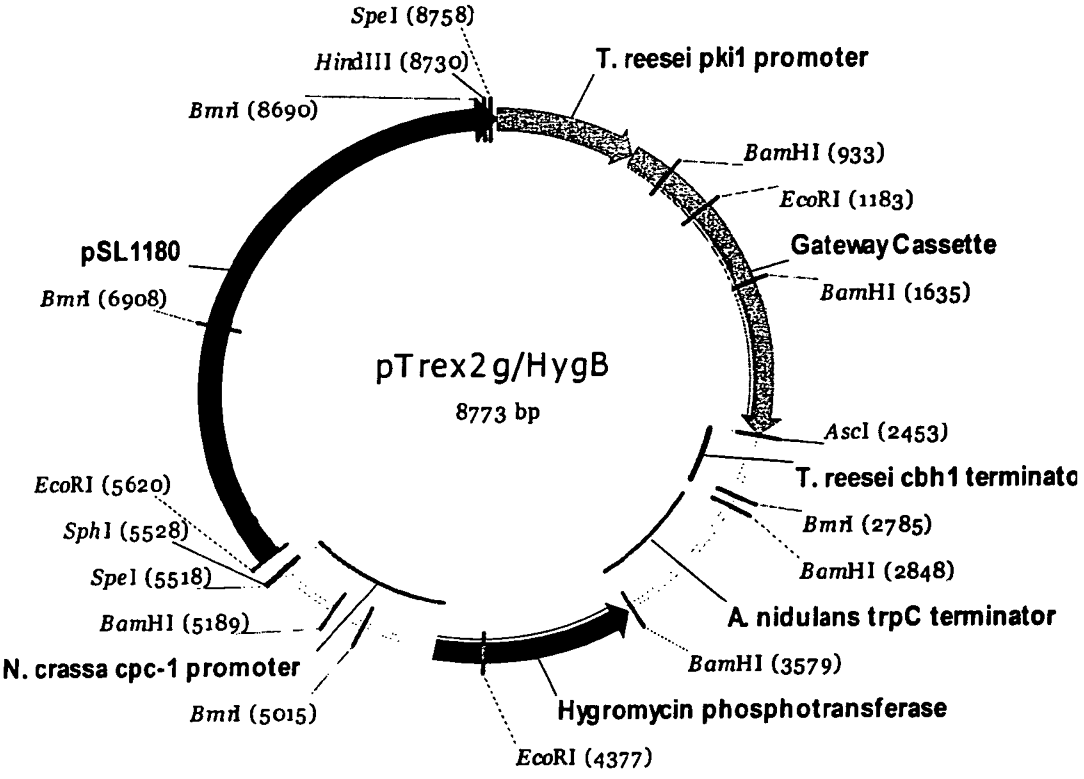
FIG. 1 depicts a Gateway compatible vector for expression cloning in *Trichoderma reesei* (pTrex2g/HygB).

The term "promoter" is defined herein as a nucleic acid that directs transcription of a downstream polynucleotide in a cell. In certain cases, the polynucleotide may contain a coding sequence and the promoter may direct the transcription of the coding sequence into translatable RNA.

The term "isolated" as defined herein means a compound, a protein, cell, nucleic acid sequence or amino acid that is removed from at least one component with which it is naturally associated.

The term "% homology" is used interchangeably herein with the term "% identity" herein and refers to the level of nucleic acid or amino acid sequence identity between the nucleic acid sequences, when aligned using a sequence alignment program. For example, as used herein, 80% homology means the same thing as 80% sequence identity determined by a defined algorithm, and accordingly a homologue of a given sequence has greater than 80% sequence identity over a length of the given sequence. Exemplary levels of sequence identity include, but are not limited to, 80, 85, 90, 95, 98% or more sequence identity to a given sequence. The term "coding sequence" is defined herein as a nucleic acid that, when placed under the control of appropriate control sequences including a promoter, is transcribed into mRNA which can be translated into a polypeptide. A coding sequence may contain a single open reading frame, or several open reading frames separated by introns, for example. A coding sequence may be cDNA, genomic DNA, synthetic DNA or recombinant DNA, for example. A coding sequence generally starts at a start codon (e.g., ATG) and ends at a stop codon (e.g., UAA, UAG and UGA).

The term "recombinant" refers to a polynucleotide or polypeptide that does not naturally occur in a host cell. A recombinant molecule may contain two or more naturally occurring sequences that are linked together in a way that does not occur naturally.

The term "heterologous" refers to elements that are not normally associated with each other. For example, if a recombinant host cell produces a heterologous protein, that protein is not produced in a wild-type host cell of the same type, a heterologous promoter is a promoter that is not present in nucleic acid that is endogenous to a wild type host cell, and a promoter operably linked to a heterologous coding sequence is a promoter that is operably linked to a coding sequence that it is not usually operably linked to in a wild-type host cell.

The term "operably linked" refers to an arrangement of elements that allows them to be functionally related. For example, a promoter is operably linked to a coding sequence if it controls the transcription of the sequence, and a signal sequence is operably linked to a protein if the signal sequence directs the protein through the secretion system of a host cell.

The term "nucleic acid" and "polynucleotide" are used interchangeably and encompass DNA, RNA, cDNA, single stranded or double stranded and chemical modifications thereof. Because the genetic code is degenerate, more than one codon may be used to encode a particular amino acid, and the present invention encompasses all polynucleotides, which encode a particular amino acid sequence.

The term "DNA construct" as used herein means a nucleic acid sequence that comprises at least two DNA polynucleotide fragments.

The term "signal sequence" refers to a sequence of amino acids at the N-terminal portion of a protein, which facilitates the secretion of the mature form of the protein outside the cell. The mature form of the extracellular protein lacks the signal sequence which is cleaved off during the secretion process.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Expression vectors may include regulatory sequences such as promoters, signal sequences, coding sequences and transcription terminators.

An "expression vector" as used herein means a DNA construct comprising a coding sequence that is operably linked to suitable control sequences capable of effecting expression of a protein in a suitable host. Such control sequences may include a promoter to effect transcription, an optional operator sequence to control transcription, a sequence encoding suitable ribosome binding sites, enhancers and sequences which control termination of transcription and translation.

As used herein, the terms "polypeptide" and "protein" are used interchangeably and include reference to a polymer of any number of amino acid residues. The terms apply to amino acid polymers in which one or more amino acid residue is an artificial chemical analog of a corresponding naturally occurring amino acid, as well as to naturally occurring amino acid polymers. The terms also apply to polymers containing conservative amino acid substitutions such that the polypeptide remains functional.

A "host" refers to a suitable host for an expression vector comprising a DNA construct encoding a desired protein. A host may be any cell type.

The term "filamentous fungi" refers to all filamentous forms of the subdivision Eumycotina (See, Alexopoulos, C. J. (1962), INTRODUCTORY MYCOLOGY, Wiley, New York). These fungi are characterized by a vegetative mycelium with a cell wall composed of chitin, glucans, and other complex polysaccharides. The filamentous fungi of the present teachings are morphologically, physiologically, and genetically distinct from yeasts. Vegetative growth by filamentous fungi is by hyphal elongation and carbon catabolism is obligatory aerobic.

A "heterologous" nucleic acid construct or sequence has a portion of the sequence which is not native to the cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, transformation, microinjection, electroporation, or the like. A "heterologous" nucleic acid construct may contain a control sequence/DNA coding sequence combination that is the same as, or different from a control sequence/DNA coding sequence combination found in the native cell.

The present teachings are based on the discovery that protein secretion in a host can be modulated by a group of chaperones and/or foldases. Accordingly the present teachings provide methods for increasing protein secretion in a host, e.g., filamentous fungi by co-expressing certain chaperone(s) and/or foldase(s). The present teachings also provide expression hosts, e.g., filamentous fungi containing certain chaperone(s) and/or foldase(s) and a polypeptide of interest for increased secretion.

According to one aspect of the present teachings, it provides methods for increasing the secretion of a polypeptide of interest in a host by expressing a secretion enhancing protein along with the desired polypeptide in the host. The secretion enhancing protein of the present teachings can be any suitable protein associated with protein folding and/or secretion. In some embodiments, the secretion enhancing protein of the present teachings can be a member of chaperone or foldase protein family. In some embodiments, the secretion enhancing protein can be a member of chaperone or foldase protein family of the host origin. In some embodiments, the secretion enhancing protein includes a combination of a chaperone protein and a foldase protein. In some embodiments, the secretion enhancing protein can be a fragment of a chaperone or foldase protein with substantially the same protein secretion enhancing function as the full-length chaperone or foldase.

In various embodiments, the secretion enhancing protein of the present teachings can be bip1, clx1, ero1, lhs1, prp3, prp4, prp1, tig1, pdi1, ppi1, ppi2, Scj1, erv2, EDEM, and/or sil1 or combinations thereof. In the context of the present teachings, the name of any particular chaperone or foldase means that particular chaperone or foldase from any species, native or recombinant, or any particular chaperone or foldase with an amino acid sequence identical or substantially identical, e.g., at least 50%, 60%, 70%, 80%, 90%, or 95% identical to the corresponding chaperone or foldase sequence illustrated in the present application, or any polypeptide that can be a homolog of that particular chaperone or foldase, e.g., based on function or structure similarities commonly accepted by one skilled in the art. Examples of nucleic acid and polypeptide sequences of bip1, clx1, ero1, lhs1, prp3, prp4, prp1, tig1, pdi1, ppi1, ppi2, Scj1, erv2, EDEM, and sil1 are illustrated in the present application as SEQ ID NOs. 1-30 (see Table 1).

TABLE 1

Exemplary nucleic acid and polypeptide sequences of secretion enhancing proteins.

| Protein | Exemplary Nucleotide Acid Sequence | Exemplary Polypeptide Sequence |
|---|---|---|
| bip1 | SEQ ID NO: 1 | SEQ ID NO: 16 |
| clx1 | SEQ ID NO: 2 | SEQ ID NO: 17 |
| ero1 | SEQ ID NO: 3 | SEQ ID NO: 18 |
| lhs1 | SEQ ID NO: 4 | SEQ ID NO: 19 |
| prp3 | SEQ ID NO: 5 | SEQ ID NO: 20 |
| prp4 | SEQ ID NO: 6 | SEQ ID NO: 21 |
| prp1 | SEQ ID NO: 7 | SEQ ID NO: 22 |
| tig1 | SEQ ID NO: 8 | SEQ ID NO: 23 |

TABLE 1-continued

Exemplary nucleic acid and polypeptide sequences of secretion enhancing proteins.

| Protein | Exemplary Nucleotide Acid Sequence | Exemplary Polypeptide Sequence |
|---|---|---|
| pdi1 | SEQ ID NO: 9 | SEQ ID NO: 24 |
| ppi1 | SEQ ID NO: 10 | SEQ ID NO: 25 |
| ppi2 | SEQ ID NO: 11 | SEQ ID NO: 26 |
| Scj1 | SEQ ID NO: 12 | SEQ ID NO: 27 |
| erv2 | SEQ ID NO: 13 | SEQ ID NO: 28 |
| EDEM | SEQ ID NO: 14 | SEQ ID NO: 29 |
| sil1 | SEQ ID NO: 15 | SEQ ID NO: 30 |

In general, the secretion enhancing protein of the present teachings can be co-expressed along with one or more desired polypeptides, e.g., polypeptides of interest in a host. The expression of the secretion enhancing protein can be under any suitable promoter known or later discovered in the art. In some embodiments, the secretion enhancing protein can be expressed under a promoter native to the host. In some embodiments, the secretion enhancing protein can be expressed under a heterologous promoter. In some embodiments, the secretion enhancing protein can be expressed under a constitutive or inducible promoter.

As used herein, the term "promoter" refers to a nucleic acid sequence that functions to direct transcription of a downstream gene. A promoter can include necessary nucleic acid sequences near the start site of transcription, such as, in the case of a polymerase II type promoter, a TATA element. The promoter together with other transcriptional and translational regulatory nucleic acid sequences, collectively referred to as regulatory sequences controls the expression of a gene. In general, the regulatory sequences include, but are not limited to, promoter sequences, ribosomal binding sites, transcriptional start and stop sequences, translational start and stop sequences, and enhancer or activator sequences. The regulatory sequences will generally be appropriate to and recognized by the host in which the downstream gene is being expressed.

A constitutive promoter is a promoter that is active under most environmental and developmental conditions. An inducible or repressible promoter is a promoter that is active under environmental or developmental regulation. Promoters can be inducible or repressible by changes in environment factors such as, but not limited to, carbon, nitrogen or other nutrient availability, temperature, pH, osmolarity, the presence of heavy metal, the concentration of an inhibitor, stress, or a combination of the foregoing, as is known in the art. Promoters can be inducible or repressible by metabolic factors, such as the level of certain carbon sources, the level of certain energy sources, the level of certain catabolites, or a combination of the foregoing, as is known in the art.

Suitable non-limiting examples of promoters include cbh1, cbh2, egl1, egl2, egl3, egl4, egl5, xyn1, and xyn2, repressible acid phosphatase gene (phoA) promoter of *P. chrysogenum* (see Graessle et al., Applied and Environmental Microbiology (1997), 63(2), 753-756), glucose-repressible PCK1 promoter (see Leuker et al. Gene (1997), 192(2), 235-240), maltose-inducible, glucose-repressible MRP1 promoter (see Munro et al. Molecular Microbiology (2001), 39(5), 1414-1426), methionine-repressible MET3 promoter (see Liu et al. Eukaryotic Cell (2006), 5(4), 638-649).

In some embodiments of the present teachings, the promoter in the reporter gene construct is a temperature-sensitive promoter. Preferably, the activity of the temperature-sensitive promoter is repressed by elevated temperature. In some embodiments, the promoter is a catabolite-repressed promoter. In some embodiments, the promoter is repressed by changes in osmolarity. In some embodiments, the promoter is inducible or repressible by the levels of polysaccharides, disaccharides, or monosaccharides.

An example of an inducible promoter useful in the present teachings is the cbh1 promoter of *Trichoderma reesei*, the nucleotide sequence of which is deposited in GenBank under Accession Number D86235. Other exemplary promoters are promoters involved in the regulation of genes encoding cellulase enzymes, such as, but not limited to, cbh2, egl1, egl2, egl3, egl5, xyn1 and xyn2.

According to the present teachings, the secretion enhancing protein can be used to increase the secretion of any suitable polypeptide in a host. In some embodiments, the polypeptide can be a heterologous polypeptide. In some embodiments, the polypeptide can be a secretable polypeptide. For example, a secretable polypeptide can be a protein or polypeptide usually secreted outside of a cell or a protein or polypeptide operably linked to a signal sequence, e.g., an amino acid sequence tag leading proteins or polypeptides through the secretion pathway of a cell. Usually any suitable signal sequence known or later discovered can be used including, without any limitation, signal sequences derived from preprochymosin, e.g., bovine preprochymosin, glucoamylase, e.g., *A. niger* glucoamylase, aspartic protease, e.g., *Rhizomucor miehei* or *Trichoderma reesei* aspartic proteases or cellulases, e.g., *Trichoderma reesei* cellobiohydrolase I, cellobiohydrolase II, endoglucanase I, endoglucanase II or endoglucanase III.

In some embodiments, the polypeptide of interest can be a member of the aspartic proteinase family, e.g., family A1 of aspartic proteinases according to the MEROPS classification (Rawlings et al., Nucleic Acids Res (2006) 34: D270-72). This protein family contains endopeptidases with a catalytic center formed by two aspartic acid residues that are active at acidic pH. Chymosins (peptidase 3.4.23.4 by the NC-IUMB classification) are aspartic proteases that perform limited digestion of kappa-casein in neonatal gastric digestion. Bovine chymosin is used to clot milk during cheese making. In some embodiments, the polypeptide of interest can be a member of chymosin family, e.g. chymosin of any species including, without any limitation, chymosin of bovine, sheep, or goat origin. In some embodiments, the polypeptide of interest can be a modified chymosin, e.g., chymosin modified, such as mutated, to increase its function in any cheese making or milk coagulation process or optimize its expression in expression hosts. In some embodiments, the polypeptide of interest can be a fusion chymosin including at least two chymosins from two different species. In the context of the present application, the term "chymosin" means chymosin of any species, native or recombinant, or any polypeptide with substantially the same amino acid sequence as chymosin, e.g., any polypeptide having at least 60%, 70%, 80%, 90%, or 95% sequence identity of a chymosin, or any polypeptide with substantially the same protein folding characteristics of a chymosin, or a chymosin homolog, e.g., based on function or structure similarities commonly accepted by one skilled in the art. In some embodiments, the heterologous protein can be any protein expressible in a filamentous fungal host. Examples of proteins expressible in filamentous fungal hosts include, but are not limited to, laccases, endopeptidases, glucoamylases, alpha-amylase, granular starch hydrolyzing enzyme, cellulases, lipases, xylanases, cutinases, hemicellulases, proteases, oxidases, and combinations thereof. In general, the expression of a desired polypeptide in the present teachings can be under any suitable promoter known or later discovered in the art. In some embodiments, the polypeptide of interest in the present teachings can be expressed under a promoter native to the host. In some embodiments, the polypeptide of interest in the present teachings can be expressed under a heterologous promoter. In some embodiments, the polypeptide of interest in the present teachings can be expressed under a constitutive or inducible promoter. In some embodiments, the polypeptide of interest in the present teachings can be expressed in a *Trichoderma* expression system with a cellulase promoter, e.g., cbh1 promoter.

According to the present teachings, the secretion enhancing protein can be used in any host, e.g., expression host to increase the secretion of a desired polypeptide in the host. For example, the expression hosts of the present teachings can be filamentous fungi. In general, the "filamentous fungi" of the present teachings are eukaryotic microorganisms and include all filamentous forms of the subdivision Eumycotina. These fungi are characterized by a vegetative mycelium with a cell wall composed of chitin, beta-glucan, and other complex polysaccharides. In various embodiments, the filamentous fungi of the present teachings are morphologically, physiologically, and genetically distinct from yeasts. In some embodiments, the filamentous fungi of the present teachings include, but are not limited to the following genera: *Aspergillus, Acremonium, Aureobasidium, Beauveria, Cephalosporium, Ceriporiopsis, Chaetomium paecilomyces, Chrysosporium, Claviceps, Cochiobolus, Cryptococcus, Cyathus, Endothia, Endothia mucor, Fusarium, Gilocladium, Humicola, Magnaporthe, Myceliophthora, Myrothecium, Mucor, Neurospora, Phanerochaete, Podospora, Paecilomyces, Penicillium, Pyricularia, Rhizomucor, Rhizopus, Schizophylum, Stagonospora, Talaromyces, Trichoderma, Thermomyces, Thermoascus, Thielavia, Tolypocladium, Trichophyton, Trametes*, and *Pleurotus*. In some embodiments, the filamentous fungi of the present teachings include, but are not limited to the following: *A. nidulans, A. niger, A. awamori*, e.g., NRRL 3112, ATCC 22342 (NRRL 3112), ATCC 44733, ATCC 14331 and strain UVK 143f, *A. oryzae*, e.g., ATCC 11490, *N. crassa, Trichoderma reesei*, e.g. NRRL 15709, ATCC 13631, 56764, 56765, 56766, 56767, and *Trichoderma viride*, e.g., ATCC 32098 and 32086.

According to another aspect of the present teachings, it provides an expression host expressing a secretion enhancing protein and a desired polypeptide, e.g., polypeptide of interest. In some embodiments, the expression host of the present teachings contains a first polynucleotide encoding a secretion enhancing protein and a second polynucleotide encoding a polypeptide of interest. In some embodiments, the expression host of the present teachings contains a first polynucleotide encoding a secretion enhancing protein, a second polynucleotide encoding a polypeptide of interest, and a third polynucleotide encoding a secretion enhancing protein, e.g., different from the one encoded by the first polynucleotide.

In some embodiments, the expression host of the present teachings contains a first polynucleotide encoding a secretion enhancing protein that can be a chaperone or foldase protein and a second polynucleotide encoding a polypeptide of interest. In some embodiments, the expression host of the present teachings contains a first polynucleotide encoding a secretion enhancing protein that can be a chaperone, a second polynucleotide encoding a polypeptide of interest, and a third polynucleotide encoding a secretion enhancing protein that can be a foldase.

According to the present teachings, the first, second, and/or third polynucleotide in the expression host of the present teachings can be operably linked to one or more promoters, e.g., native or heterologous promoters of the expression host.

Any suitable promoter can be used in the present teachings. In some embodiments, the promoter operably linked to the first and/or third polynucleotide can be a constitutive or inducible promoter. In some embodiments, the promoter operably linked to the second polynucleotide can be a promoter native to the expression host containing the second polynucleotide. In some embodiments, the promoter operably linked to the second polynucleotide can be a native promoter associated with any gene characteristic of active transcription or expression in the expression host. In some embodiments, the promoter operably linked to the second polynucleotide can be a modified native promoter, e.g., mutated native promoter with enhanced transcription activity of the promoter. In some embodiments, the promoter operably linked to the second polypeptide in a *Trichoderma* expression system can be a cellulase promoter, e.g., cbh1 promoter.

In some embodiments the desired polypeptide may be produced as a fusion polypeptide. In some embodiments the desired polypeptide may be fused to a polypeptide that is efficiently secreted by a filamentous fungus. In some embodiments the desired polypeptide may be fused to a CBHI polypeptide, or portion thereof. In some embodiments the desired polypeptide may be fused to a CBHI polypeptide, or portion thereof, that is altered to minimize or eliminate catalytic activity. In some embodiments the desired polypeptide may be fused to a polypeptide to enhance secretion, facilitate subsequent purification or enhance stability.

In general, the first, second, and/or third polynucleotide in the expression host of the present teachings can be either genetically inserted or integrated into the genomic makeup of the expression host, e.g., integrated into the chromosome of the expression host, or existing extrachromosomally, e.g., existing as a replicating vector within the expression host under selection condition for a selection marker carried by the vector.

According to the present teachings, the secretion level of a desired polypeptide in the expression host of the present teachings can be determined by various factors, e.g., growth conditions of the host, etc., however normally higher than the secretion level of the desired polypeptide expressed in the host without the expression of a secretion enhancing protein. In some embodiments, the secretion level of a desired polypeptide, e.g., bovine chymosin in the expression host of the present teachings, e.g., *T. reesei* can be at least 1 mg/liter, 2 mg/liter, 3 mg/liter, 4 mg/liter, or 5 mg/liter when the host grows in a batch fermentation mode in a shake flask, or at least 50 mg/liter, 100 mg/liter, 150 mg/liter, 200 mg/liter, 250 mg/liter, or 300 mg/liter when the host grows in a fermenter environment with controlled pH, feed-rate, etc. e.g., fed-batch fermentation.

In general, the secretion level of a polypeptide can be evaluated via various assays. For example, in order to evaluate the expression and/or secretion of a secretable polypeptide, assays can be carried out at the protein level, the RNA level or by use of functional bioassays particular to secretable polypeptide activity and/or production. Exemplary assays employed to analyze the expression and/or secretion of secretable polypeptide include, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production, expression and/or secretion of a secretable polypeptide can be measured in a sample directly, for example, by assays for enzyme activity, expression and/or production. Protein expression, may be evaluated by immunological methods, such as immunohistochemical staining of cells, tissue sections or immunoassay of tissue culture medium, e.g., by Western blot or ELISA. Such immunoassays can be used to qualitatively and quantitatively evaluate expression of secretable polypeptide. The details of such methods are known to those of skill in the art and many reagents for practicing such methods are commercially available.

According to yet another aspect of the present teachings, it provides extracts, e.g., solids or supernatant obtained from the culture of the expression host of the present teachings. In some embodiments, the supernatant does not contain substantial amount of the expression host, in some embodiments, the supernatant does not contain any amount of the expression host.

EXAMPLES

Aspects of the present teachings may be further understood in light of the Examples, which should not be construed as limiting the present teachings in any way.

Example 1

Vector for Over-Expression of bip1 in *T. reesei*

A Gateway-compatible expression vector, pTrex2g/hygB, was designed to enable over-expression of the *T. reesei* chaperone gene bip1. After insertion into pTrex2g/hygB the open reading frame of the bip1 gene was flanked by the promoter sequences of the *T. reesei* pki1 gene and the terminator sequences of the *T. reesei* cbh1 gene. The vector also contained the *E. coli* hygromycin phosphotransferase (hph) gene flanked by the promoter sequences of the *Neurospora crassa* cpc-1 gene and the terminator sequences of the *Aspergillus nidulans* trpC gene.

The following segments of DNA were assembled in the construction of Trex2g/HygB (see FIG. 1):

A 728 bp fragment of *T. reesei* genomic DNA representing the promoter region from the pki1 (pyruvate kinase) gene. At the 5' end of this DNA were 6 bp of synthetic DNA representing a SpeI restriction site and at the 3' end were 6 bp of synthetic DNA adding a SacII restriction site.

The 1714 bp Gateway cassette to allow insertion of the chaperone or foldase sequence using Gateway cloning technology (InVitrogen Corporation, USA). This cassette has the following components; the 125 bp *E. coli* attR1 phage λ attachment site, a chloramphenicol resistance gene, the *E. coli* ccdB gene and the 125 bp *E. coli* attR2 phage λ attachment site.

The Gateway cassette was followed by a 17 bp fragment of synthetic DNA ending with an AscI site. The native *T. reesei* cbh1 terminator region (356 bp) immediately followed the AscI site. This terminator region ended with 4 bp of synthetic DNA being the half of a PmeI restriction site (GTTT) remaining after digestion.

A 2.6 kb cassette consisting of the *Neurospora crassa* cpc-1 promoter fused to the *E. coli* hph open reading frame followed by the *Aspergillus nidulans* trpC terminator. This cassette was amplified by PCR from the vector pFAC1 described by Barreau et al. (1998). The PCR product had 55 bp of synthetic DNA (part of a multiple cloning site) at one end and was blunt-end ligated to the digested PmeI site at the end of the cbh1 terminator. At the other end the PCR product had 20 bp of synthetic DNA terminating in a SphI site that was digested to link with pSL1180 below.

The above DNA fragments were inserted in the *E. coli* vector pSL1180 between the SpeI and SphI sites of the multiple cloning sites.

Example 2

The *Trichoderma reesei* Chymosin Production Strain CHY1-2

A synthetic version of the bovine prochymosin B open reading frame (see FIG. 2, SEQ ID NO: 42) was constructed with codon usage optimized for expression in *Trichoderma*. A vector, pTrex4-ChyGA was designed for the expression of an open reading frame encoding a fusion protein that consists of the following components from the amino-terminus: the *T. reesei* CBHI secretion signal sequence, the *T. reesei* CBHI catalytic core and linker region, and the bovine prochymosin B protein. This open reading frame is flanked by the promoter and terminator sequences of the *T. reesei* cbh1 gene. The vector also contains the *Aspergillus nidulans* amdS gene, encoding acetamidase, as a selectable marker for transformation of *T. reesei.*

Figure 3:
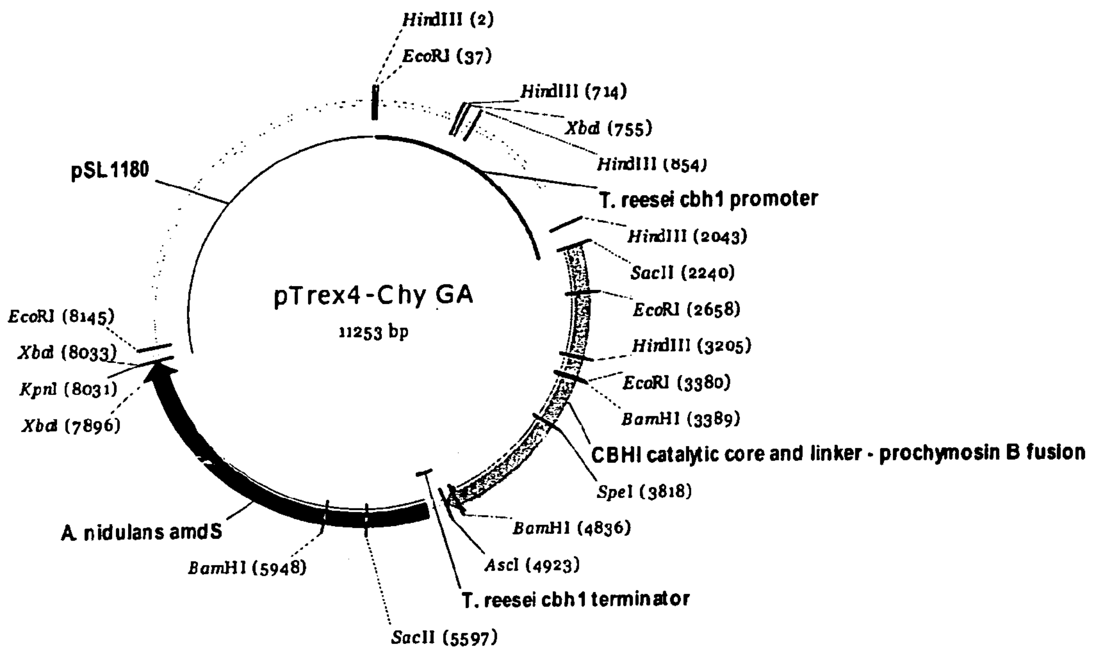
FIG. 3 depicts a CBH1-prochymosin B expression vector, pTrex4-CHYGA.

The following segments of DNA were assembled in the construction of pTrex4-ChyGA (see FIG. 3):

The *T. reesei* cbh1 promoter and coding region. This DNA sequence begins at a naturally occurring HindIII site approximately 2250 bp upstream of the coding region. It ends at a SpeI site created at the end of the sequence encoding the CBHI linker region by changing the codon for the threonine residue at position 478 of preCBHI from ACC to ACT and adding AGT nucleotides immediately afterwards.

The synthetic coding region for bovine prochymosin B was directly fused to the end of the CBHI coding region. The sequence of this DNA is shown in FIG. 2. Immediately after the prochymosin B stop codon are 8 nucleotides of synthetic DNA representing an AscI restriction site (GGCGCGCC).

The native *T. reesei* cbh1 terminator region (356 bp) immediately followed the above AscI site.

A 2.75 kb fragment of *Aspergillus nidulans* genomic DNA including the promoter, coding region and terminator of the amdS (acetamidase) gene. This is a blunt-ended fragment generated by digestion with SspI at naturally occurring restriction sites The above DNA fragments were inserted in the *E. coli* vector pSL1180 (Pharmacia) between the HindIII and StuI sites of the multiple cloning site.

Plasmid pTrex4-CHY GA was inserted into the *Trichoderma reesei* Morph1 1.1 pyr4+, a strain derived from RL-P37 (Sheir-Neiss, G. and Montenecourt, B. S., 1984, Appl. Microbiol. Biotechnol. 20:46-53) and deleted for the cbh1, cbh2, egl1, and egl2 genes described by Bower et al (Carbohydrases from *Trichoderma reesei* and other micro-organisms, Royal Society of Chemistry, Cambridge, 1998, p. 327-334) by polyethylene glycol (PEG)-mediated transformation of protoplasts. Transformants were selected on agar medium containing acetamide as sole nitrogen source. This resulted in the chymosin production host strain *T. reesei* CHY1-2.

Example 3

Cloning the *T. reesei* bip1 Gene and Insertion into pTrex2g/hygB

In order to insert the *T. reesei* bip1 gene into pTrex2g/HygB the DNA sequence was amplified by PCR using attB PCR primers. The forward primer (F-attB1) had the following sequence at the 5' end, 5'-GGGGACAAGTTTGTACAAAAAAGCAGGCT-3' (SEQ ID NO:43), followed by a sequence specific to the 5' end of the bip1 open reading frame. The reverse primer (R-attB2) had the following sequence at the 5' end, 5'-GGGGACCACTTTGTACAAGAAAGCTGGGT-3' (SEQ ID NO:44), followed by a sequence specific to the 3' end of the bip1 open reading frame. The full sequence of the two primers was:

```
                                      (SEQ ID NO: 31)
5'-GGGGACAAGTTTGTACAAAAAAAGGCTATGGCTCGTTCACGGAGCTC
CC-3'

                                      (SEQ ID NO: 32)
5'-GGGGACCACTTTGTACAAGAAAGCTGGGTTTACAATTCGTCGTGGAA
GTCGCC-3'
```

The bip1 gene was amplified using Phusion polymerase from Finnzymes (Cat. No. F-530) according to the manufacturer's directions. The PCR mixture contained 1 μl *T. reesei* genomic DNA, 10 μl 5× buffer HF, 1 μl of 10 mM dNTPs, 1.5 μl DMSO, 0.5 μl Phusion DNA polymerase, 2 μl each of the forward and reverse bip1 primers and 32 μl MilliQ H2O. The following temperature and time conditions were used for the PCR. Denaturation of DNA at 98° C. for 30 sec followed by 30 cycles at 98° C. for 10 sec, 55° C. for 30 sec and 72° C. for 90 sec, and a final extension at 72° C. for 10 min.

After agarose gel electrophoresis the 2.3 kb PCR product was purified using a Qiagen gel extraction kit (Cat. No. 28706) according to the manufacturers instructions. The purified PCR product was inserted into the vector pDONR201 (Invitrogen; Cat. No. 11798014) using a BP Clonase reaction (Invitrogen; Cat. No. 11789013) according the following protocol. The following components were mixed; 2 μl pDONR201, 4 μl PCR product, 4 μl BP Enzyme buffer, 6 μl TE buffer, and 4 μl BP Enyzme. After overnight incubation at 25° C. the reaction was stopped by adding Proteinase K solution and incubating for 10 minutes at 37° C. 2 μl of the reaction mixture was used for transformation of *E. coli* TOP10 chemical competent cells (Invitrogen Cat. No. C4040-10) according to the manufacturer's directions. After sequence analysis, the bip1 sequence was transferred to the expression vector pTrex2g/hygB using the LR Clonase reaction (Invitrogen; Cat. No. 11791019) according to the following protocol. The following components were mixed. 2 μl pDON201R with inserted bip1 gene, 2 μl pTrex2g/hygB, 4 μl LR enzyme buffer, 4 μl LR enzyme mix, and 8 μl TE. Following overnight incubation at 25° C. the reaction was stopped by addition of Proteinase K solution and incubation for 10 minutes at 37° C. 2 μl of the reaction mixture was transformed into *E. coli* MAX EFFICIENCY DH5α Competent Cells (Invitrogen; Cat. No. 18258012). Plasmid DNA, pTrex2g/HygB/bip1 was isolated from two resulting *E. coli* colonies for transformation of *T. reesei* CHY1-2

Example 4

*Trichoderma* Transformation

Expression vector pTrex2g/HygB/bip1 was inserted into spores of *T. reesei* CHY1-2 using a biolistic transformation procedure. DNA-coated tungsten particles were prepared as follows. 60 mg of M10 tungsten particles were added to 1 ml ethanol (70% or 100%) in a microcentrifuge tube. This mixture was allowed to soak for 15 minutes, followed by centrifugation for 15 min at 15,000 rpm. The supernatant was then decanted and the pellet washed three times with sterile distilled water. The majority of the distilled water was removed after the final wash. The pellet was then resuspended in 1 ml of a 50% glycerol (v/v, sterile) solution. While continuously vortexing a 25 μl aliquot of this particle suspension was removed and placed in a microcentrifuge tube. To this tube the following components were added (while continuously vortexing) in the following order. 0.5-5 μl of pTrex2g/HygB/bip1 DNA solution (1 μg/μl), 25 μl 2.5M $CaCl_2$, and 10 μl 0.1M spermidine The mixture was allowed to coat the particles for 5-15 minutes during continuous vortexing, and was used as soon as possible to avoid tungsten degradation of the DNA. The mixture was then centrifuged for approximately three seconds. The supernatant was then removed and the pellet was washed with approx 200 μl of 70% ethanol (v/v) followed by a 3 second centrifugation and removal of the supernatant. The pellet was again washed with 200 μl of 100% ethanol, followed by another 3 second centrifugation. The supernatant was removed and the pellet was then resuspended in 24 μl 100% ethanol and mixed by pipetting. 8 μl aliquots were placed onto macrocarrier discs (Bio-Rad, Hercules, Calif.) by pipetting the aliquots in the exact center of the disks while the disks were in a desiccator. The discs were kept in a desiccator until thoroughly dry and kept there until immediately before use. The macrocarrier discs were inserted into a Model PDS-1000/He Biolistic Particle Delivery System (Bio-Rad, Hercules, Calif.). This apparatus was used according to the manufacturer's directions to propel the DNA-coated tungsten particles at the *T. reesei* spores prepared as below.

A spore suspension of strain CHY1-2 was made with approximately $5\times10^8$ spores/ml. 100-200 μl aliquots of the spore suspension was spread over an area approximately 6 cm in diameter at the center of a plate of agar medium containing acetamide as sole nitrogen source. After the biolistic transformation, the plates were placed in a 25° C. incubator for 1 day. Then, 1 ml Hygromycin B solution (4 mg/ml) was spread onto the plates and an additional incubation of 3 days at 28° C. was performed. Transformants were transferred onto fresh agar plates with acetamide as sole nitrogen source and Hygromycin B (200 μl/ml), and placed at 28° C.

Example 5

Chymosin Expression in Shake Flasks

Lactose defined liquid medium contained the following components. Casamino acids, 9 g/L; (NH4) 2SO4, 5 g/L; MgSO4.7H2O, 1 g/L; KH2PO4, 4.5 g/L; CaCl2.2H2O, 1 g/L, PIPPS, 33 g/L, 400× *T. reesei* trace elements, 2.5 ml/L; pH adjusted to 5.5 with NaOH. After sterilization, lactose was added to a final concentration of 20% v/v.

400× *T. reesei* trace elements solution contained the following: citric Acid (anhydrous), 175 g/L; FeSO4.7H2O, 200 g/L, ZnSO4.7H2O, 16 g/L, CuSO4.5H2O, 3.2 g/L; MnSO4.H2O, 1.4 g/L; H3BO3, 0.8 g/L.

Ten transformants of *T. reesei* strain CHY1-2 with the bip1 expression vector were evaluated by shake flask culture in lactose defined liquid medium for improved chymosin production. From each morphologically stable transformant colony on a Petri dish one square cm was excised and used to inoculate a single 30 ml LD medium in a baffled shake flask. After 3 days of growth at 28° C. and 150 rpm, 5 ml of this pre-culture was used to inoculate 45 ml LD medium in a baffled shake flask. This production culture was grown for 3 days at 28° C. and 150 rpm. Supernatants were collected by centrifugation of the fermentation broth. Chymosin activity was measured and SDS-PAGE and Western analysis were performed to determine the chymosin concentration.

The chymosin activity in the culture supernatant was measured using essentially the same methods as previously described (Dunn-Coleman et al., 1991, Bio/Technology 9:976-981). Two transformants, bip1 #1.2 and bip1 #1.10 were chosen for further study because they showed a significant improvement in chymosin production compared to the host strain *T. reesei* CHY1-2 (see Table 2, column 2).

Culture supernatants from these two transformants were subjected to SDS-PAGE (sodium dodecyl sulfate—polyacrylamide gel electrophoresis). Following electrophoresis protein was stained with Coomassie Brilliant Blue. Based on the intensity of the 35 kDa band corresponding to mature chymosin transformants bip1 #1.2 and bip1 #1.10 produced more chymosin than strain CHY 1-2.

Four replicate shake flask cultures of bip1 #1.2, bip1 #1.10 and strain CHY 1-2 were grown and chymosin activity analysis was performed. Again, transformants bip1 #1.2 and bip1 #1.10 clearly produced more active chymosin than the host strain *T. reesei* CHY1-2 (Table 2, column 3).

TABLE 2

Percentage of chymosin activity in shake flask supernatants of transformants bip1 #1.2 and bip1 #1.10 compared to *T. reesei* CHY1-2

| Strain | % of chymosin activity (Single shake flask experiment) | % of chymosin activity (Average of four flasks) |
|---|---|---|
| CHY 1-2 | 100 | 100 |
| Bip1 #1.2 | 282 | 363 |
| Bip1 #1.10 | 240 | 370 |

Figure 4:
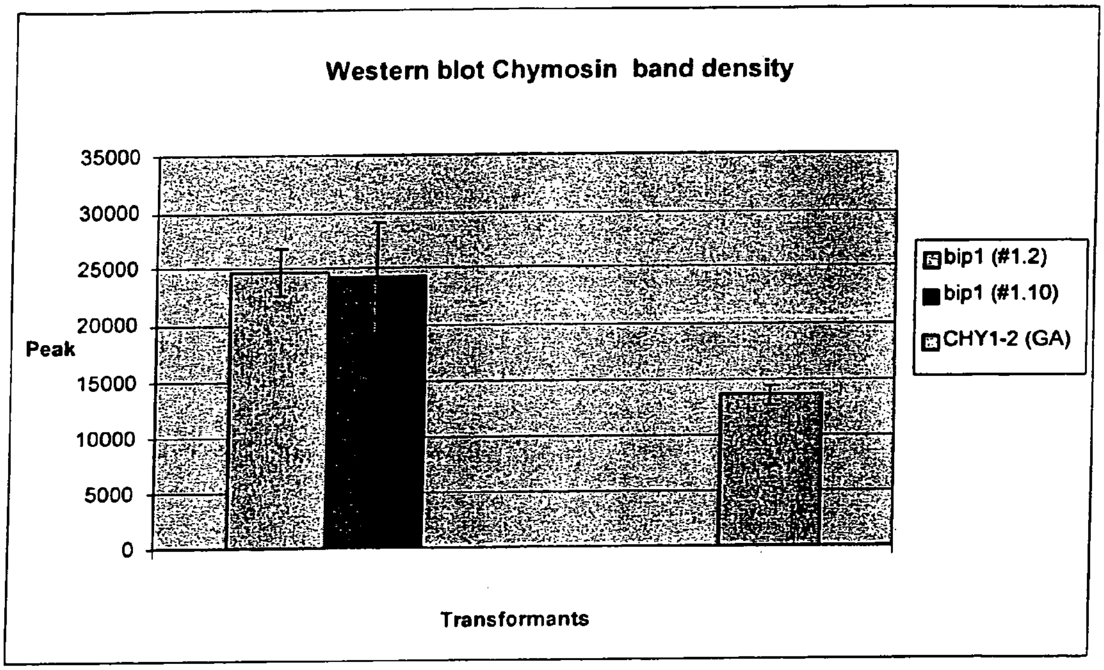
FIG. 4 depicts chymosin band density analysis of Western blots of three day shake flask culture samples.

It was possible that some secreted chymosin was present in an inactive form due to degradation. Chymosin was initially secreted as a CBHI-prochymosin fusion protein. At low pH, mature active chymosin was expected to be released by autocatalytic cleavage at the junction between the chymosin proregion and mature chymosin. Therefore, it was also possible that some chymosin was present as CBHI-prochymosin fusion protein in the culture supernatant and consequently inactive. For these reasons, Western blot analysis was performed to determine the total amount of secreted chymosin; as active, inactive and fused protein. Proteins were separated by SDS-PAGE using the NuPAGE Novex pre-cast gel system according to the manufacturer's instructions (InVitrogen, Carlsbad, Calif.). Following electrophoresis the proteins were electro-blotted onto a PVDF membrane using an XCell II Blot Module as directed by the manufacturer (InVitrogen, Carlsbad, Calif.). The BM chromogenic Western Blotting Kit from Roche (Cat. No. 1647644) was used to detect alkaline phosphatase-labeled antibodies. Primary antibodies (affinity-purified polyclonal rabbit anti-chymosin) were diluted 1000 times. The blot was scanned and the intensities of the chymosin-specific bands were measured using Total Lab Software (see FIG. 4). Based on this measure of total chymosin production, transformants bip1 #1.2 and bip1 #1.10 showed a clear increase compared to strain CHY 1-2.

Example 6 mRNA Analysis of *T. reesei* CHY 1-2 and bip1 #1.10

Shake flask fermentations were performed to collect mycelium for mRNA level analysis for chymosin, CBH1 and Bip1 in two *T. reesei* strains, CHY 1-2 and bip1 #1.10. Broth was collected after 72 hrs of culture and frozen in liquid nitrogen.

Total RNA was isolated using a FastRNA Red Kit (Bio 101, Inc., Carlsbad, Calif.) according to the manufacturer's instructions. In brief, the following protocol was used. Lysing tubes were chilled on dry ice and 500 µl CRSR RED, 500 µl PAR, and 100 ul CIA were added and frozen.

A piece of frozen mycelia (approx. 0.7 cm cubed) was added to the lysing tube with frozen reagents. The tube was placed at 60° C. for 2-5 minutes, until bottom reagents around the beads started to thaw, but not top reagents or sample. The tube was immediately secured in a FastPrep machine, and shaken for 3×30 seconds at setting 6, allowing 1 min rest between disruptions. The tubes were removed and placed on wet ice 5 min before centrifugation. The aqueous phase was drawn off to a new tube and an equal volume of CIA was added, vortexed to mix and centrifuged. The last step was repeated and an equal volume of DIPS was added, mixed and incubated at room temperature for 1-2 minutes. The tube was centrifuged to pellet the RNA and the supernatant was removed. The pellet was washed with 500 µl SEWS by adding the wash and removing immediately. The last traces of wash were removed and the pellet was air dried for 5-10 min before resuspending in 200 µl RNase-free water. 40 µl of LiCl solution was added and the sample was incubated at 4° C. overnight. The tube was centrifuged to pellet the RNA, the RNA was washed as before, and finally resuspended in 100-200 µl of RNase-free water.

Complementary DNA synthesis was performed with a High Archive cDNA synthesis kit from Applied Biosystems Inc. according to the manufacturer's directions, after which the cDNA was amplified with gene specific primers (Table 3).

TABLE 3

Gene-specific primers designed for use in TaqMan Gene Expression Assays

| Name | Sequence |
|---|---|
| CBH1 forward | AGTTACCACGAGCGGTAACAG (SEQ ID NO: 33) |
| CBH1 reverse | AAGAGAACTCGTTGCCAAGC (SEQ ID NO: 34) |
| Bip1 forward | CACCAACACCGTCTACGATG (SEQ ID NO: 35) |
| Bip1 reverse | CGTTCTTCTCAATGACCTTGTAG (SEQ ID NO: 36) |
| Chymosin forward | CAGCAAGCTCGTCGGC (SEQ ID NO: 37) |
| Chymosin reverse | GGTACATCTTGCCGTTGATCTC (SEQ ID NO: 38) |

Figure 5:
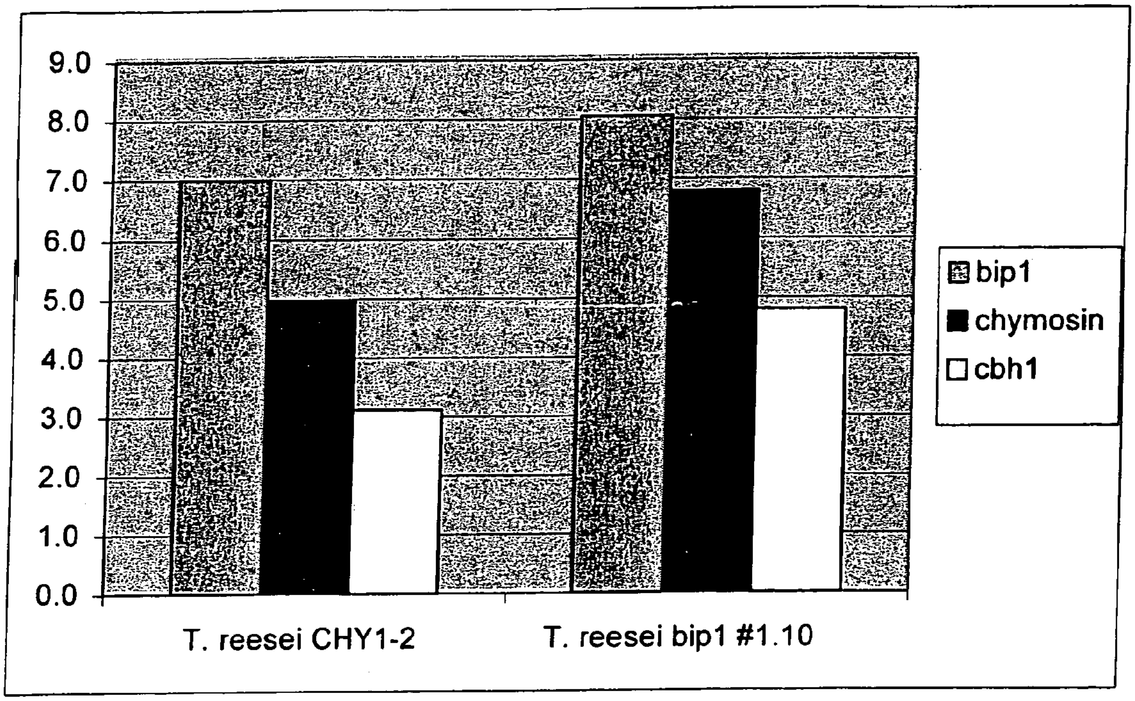
FIG. 5 depicts the levels of bip1, chymosin and cbh1 mRNA in *Trichoderma reesei* strains.

Quantification of the amplified cDNA was performed using the TaqMan Gene Expression Assay kit from Applied Biosystems, Inc. with an Applied Biosystems 7900 HT thermal cycler according the manufacturer's instructions. In brief, the TaqMan Universal PCR Master Mix, No AmpErase UNG was mixed with 20× TaqMan Gene Expression Assay Mix (containing unlabelled gene-specific primers and TaqMan MGB probe) and cDNA. The following thermal cycler conditions were then applied. Two minutes at 50° C., 10 min at 95° C., and 40 cycles of 15 sec at 95° C., 1 min at 60° C. The bip1, chymosin and cbh1 levels were determined relative to the native *T. reesei* genes, gpd1 (encoding glyceraldehyde-3-phosphate dehydrogenase) and act1 (encoding actin). For each gene, a cycle threshold value was determined. This value is equivalent to the number of PCR cycles required for a fluorescence signal to be detectable. The difference between the cycle threshold value (ΔCT) for each of bip1, chymosin or cbh1 and either gpd1 or act1 was calculated. The units on the y axis of FIG. 5 represent ΔCT and one unit increase represents a doubling of mRNA level.

The above mRNA analyses showed that bip1, chymosin and cbh1 levels are all increased as a result of bip1 over-expression in transformant bip1 #1.10 compared to strain CHY 1-2. (see FIG. 5).

Example 7

*T. reesei* Strain for Chymosin Production

A vector, pCBHIxCBD-Chy, was designed for the expression of an open reading frame encoding a fusion protein that consists of the following components from the amino-terminus: the *T. reesei* CBHI secretion signal sequence, the full-length *T. reesei* CBHI mature protein (including catalytic domain, linker region and cellulose binding domain), and the *Bos taurus* prochymosin B protein. A single codon was altered within the CBHI catalytic domain in order to inactivate the CBHI enzyme. This open reading frame is flanked by the promoter and terminator sequences of the *T. reesei* cbh1 gene. The vector also contains the *Aspergillus nidulans* amdS gene, encoding acetamidase, as a selectable marker for transformation of *T. reesei.*

The following segments of DNA were assembled in the construction of pCBHIxCBD-Chy. The *T. reesei* cbh1 promoter and coding region. This DNA sequence begins at a naturally occurring XbaI site approximately 1500 bp upstream of the coding region. The following changes to the native *T. reesei* genomic DNA sequence were made. Within the CBHI coding region the codon for amino acid 212 of the mature CBHI protein was changed from GAG (Glutamic acid) to CAG (Glutamine), known to result in production of an inactive form of CBHI (Stahlberg, J. (1996) J. Mol. Biol. 264:337-349).

Within the segment of the coding region encoding the CBHI linker region a change was made to create a SpeI restriction site. This changed the sequence from ACC CAG to ACT AGT ACC CAG (SEQ ID NO: 39) altering the amino acid sequence by insertion of two residues from Thr Gln to Thr Ser Thr Gln (SEQ ID NO:45). The Gln in this sequence represents the first amino acid of the cellulose binding domain of CBHI. At the end of the CBHI coding sequence two additional codons (ACT AGT encoding Ser Thr) were added to create a SpeI restriction site.

The synthetic coding region for bovine prochymosin B is directly fused to the end of the CBHI coding region. The sequence of this DNA, and the encoded protein, are shown in FIG. 2. Immediately after the prochymosin B stop codon are 8 nucleotides of synthetic DNA representing an AscI restriction site (GGCGCGCC).

The native *T. reesei* cbh1 terminator region (356 bp) immediately follows the above AscI site. This terminator region ends with 4 bp of synthetic DNA being the half of a PmeI restriction site (GTTT) remaining after digestion.

A 2.75 kb fragment of *Aspergillus nidulans* genomic DNA including the promoter, coding region and terminator of the amdS (acetamidase) gene. This is a blunt-ended fragment generated by digestion with SspI at naturally occurring restriction sites. A natural XbaI site occurs before the SspI site at the end of the terminator region. A 55 bp fragment of the multiple cloning site of pSL1180 from the StuI to the KpnI site.

The above DNA fragments were inserted in the *E. coli* vector pNEB193 (New England Biolabs, Inc., USA) between the XbaI and KpnI sites of the multiple cloning site. pNEB193 is identical to pUC19 (Yannisch-Perron et al., 1985) except for the addition of several restriction endonuclease sites to the multiple cloning site.

The expression vector pCBHIxCBD-Chy was digested with XbaI to release a fragment of DNA containing only the cbh1 promoter, CHI-prochymosin B coding sequence, cbh1 terminator and *A. nidulans* amdS gene. Only this XbaI fragment of DNA, not the entire pCBHIxCBD-Chy expression vector, was inserted into the *T. reesei* production strain.

In more detail, this XbaI fragment contains the following segments of DNA. The *T. reesei* cbh1 promoter and coding region. This DNA sequence begins at a naturally occurring XbaI site approximately 1500 bp upstream of the coding region. The following changes to the native *T. reesei* genomic DNA sequence were made.

Within the CBHI coding region the codon for amino acid 212 of the mature CBHI protein was changed from GAG (Glutamic acid) to CAG (Glutamine) resulting in production of an inactive form of CBHI. Within the segment of the coding region encoding the CBHI linker region a change was made to create a SpeI restriction site. This changed the sequence from ACC CAG to ACT AGT ACC CAG (SEQ ID NO:39) altering the amino acid sequence by insertion of two residues from Thr Gln to Thr Ser Thr Gln (SEQ ID NO:45). The Gln in this sequence represents the first amino acid of the cellulose binding domain of CBHI. At the end of the CBHI coding sequence two additional codons (ACT AGT encoding Ser Thr) were added to create a SpeI restriction site.

The synthetic coding region for bovine prochymosin B was directly fused to the end of the CBHI coding region. The sequence of this DNA, and the encoded protein, are shown in FIG. 2. Immediately after the prochymosin B stop codon are 8 nucleotides of synthetic DNA representing an AscI restriction site (GGCGCGCC).

The native *T. reesei* cbh1 terminator region (356 bp) immediately follows the above AscI site. This terminator region ends with 4 bp of synthetic DNA being the half of a PmeI restriction site (GTTT) remaining after digestion. A 2.75 kb fragment of *Aspergillus nidulans* genomic DNA including the promoter, coding region and terminator of the amdS (acetamidase) gene. This fragment begins at a naturally occurring SspI site and ends at a natural XbaI site.

The expression vector pTrex2g/HygB/Bip1 was described in Example 1. This vector was digested with SpeI and BmrI to release a fragment of DNA containing only the pki1 promoter, bip1 coding region, and cbh1 terminator. Only this SpeI-BmrI fragment of DNA, not the entire pTrex2g/HygB/Bip1 expression vector, was inserted into the *T. reesei* production strain. In more detail, this SpeI-BmrI fragment contains the following segments of DNA.

A 728 bp fragment of *T. reesei* genomic DNA representing the promoter region from the pki1 (pyruvate kinase) gene. At the 5' end of this DNA are 5 bp of synthetic DNA representing a digested SpeI restriction site and at the 3, end are 6 bp of synthetic DNA adding a SacII restriction site. The 25 bp *E. coli* attB1 phage λ attachment site that remains after insertion of the sequence bip1 sequence (below) using Gateway cloning technology (InVitrogen Corporation, USA). A 2.3 kb fragment of *T. reesei* genomic DNA representing only the coding region of the bip1 gene. The 25 bp *E. coli* attB2 phage λ attachment site that remains after insertion of the sequence bip1 sequence (below) using Gateway cloning technology (InVitrogen Corporation, USA) followed by a 17 bp fragment of synthetic DNA ending with an AscI site.

The native *T. reesei* cbh1 terminator region (356 bp) immediately follows the above AscI site. This terminator region ends at a naturally occurring BmrI restriction site. Plasmid pCBHIxCBD-Chy was digested with XbaI and the CBHI-prochymosin B expression cassette (with amdS gene) was purified by agarose gel electrophoresis. Plasmid pTrex2g/HygB/Bip1 was digested with SpeI and BmrI and the Bip1 expression cassette was purified by agarose gel electrophoresis. *T. reesei* strain Pent Δ (derived from strain RL-P37 with deletions in the cbh1, cbh2, egl1, egl2 and egl3 genes) was transformed with a mixture of the purified CBHI-prochymosin B and Bip1 expression cassettes using a PEG-mediated protoplast transformation protocol.

Several transformants were isolated, grown in shake flasks and examined for chymosin production. One transformant was chosen and called strain *Trichoderma reesei* Pent CHY-Bip 3. The integration of DNA in transformant Pent CHY-Bip 3 was investigated by Southern analysis to show that only the intended modifications to the *T. reesei* Pent Δ strain had been made. Chromosomal DNA was extracted (see Appendix 1) from the transformant, as well as from the host strain PentΔ. The chromosomal DNA was digested, independently, with XbaI, SpeI or StuI. The digests were purified and concentrated by ethanol precipitation. Digested DNA (5-10 ug) was subjected to electrophoresis on 1% agarose gels. DNA molecular weight markers, and expression vectors pCBHIxCBD-Chy (digested with XbaI) and pTrex2g/HygB/Bip1 (digested with BmrI), were also run on appropriate gels. Following electrophoresis, DNA was transferred to nylon membrane (Nytran SuperCharge; Schleicher & Schuell BioScience). After blotting, the membranes were hybridized with 32P-labeled pCBHIxCBD-Chy, pTrex2g/HygB/Bip1, pUC18, or a PCR product consisting of the entire Hygromycin B resistance cassette (including cpc-1 promoter, hph coding region, and trpC terminator). The latter PCR product was generated from pTrex2g/HygB/Bip1 as template using the following two primers:

```
hph1,
5' TCTCCGGTGTCCCTTGTCCCTTC-3'     (SEQ ID NO: 40)
and

hph2,
5'-ACCTGTGGCGCCGGTGATGCCGG-3'.    (SEQ ID NO: 41)
```

No hybridizing bands were observed with chromosomal DNA extracted from *T. reesei* Pent Δ or transformant Pent CHY-Bip 3 using the pUC18 probe demonstrating that no bacterial vector DNA was integrated in either of these strains. Similarly, hybridization with the Hygromycin B resistance cassette demonstrated that this DNA had not integrated in strain Pent CHY-Bip 3. The hybridization results with pCBHIxCBD-Chy and pTrex2g/HygB/Bip1 demonstrated that both the CBHI-prochymosin B expression cassette and the Bip1 expression cassette were integrated in strain Pent CHY-Bip 3. These results showed that only the intended CBHI-prochymosin B and Bip1 expression cassettes were integrated into the *T. reesei* chromosome.

What is claimed is:

1. A filamentous fungal host for production of a secretable polypeptide containing a first polynucleotide encoding a secretion enhancing protein and a second polynucleotide encoding a chymosin, wherein the secretion enhancing protein is bip1, and wherein the first polynucleotide is operably linked to a first promoter and the second polynucleotide is operably linked to a second promoter;

wherein the secretion level of the chymosin in the filamentous fungus is at least 50 mg/liter when the filamentous fungus grows in a fermentation condition.

2. The filamentous fungal host of claim 1, further comprising a third polynucleotide operably linked to a third promoter, wherein the third polynucleotide encodes a secretion enhancing protein selected from the group consisting of bip1, clx1, ero1, lhs1, prp3, prp4, prp1, tig1, pdi1, ppi1, ppi2, Scj1, erv2, EDEM, and sil1.

3. The filamentous fungal host of claim 2, wherein the third polynucleotide encodes a foldase.

4. The filamentous fungal host of claim 2, wherein the first promoter and the third promoter is a constitutive promoter.

5. The filamentous fungal host of claim 1, wherein the first promoter is a constitutive promoter.

6. The filamentous fungal host of claim 1, wherein the filamentous fungus is *T. reesei.*

7. The filamentous fungal host of claim 1, wherein the second promoter is a promoter obtained from the filamentous fungal host.

8. The filamentous fungal host of claim 1, wherein the filamentous fungus is *T. reesei* and the second promoter is a CBH1 promoter of *T. reesei.*

9. The filamentous fungal host of claim 1, wherein the second polynucleotide encodes a bovine chymosin.

10. A biologically pure culture comprising a population of filamentous fungi of claim 1.

11. A biologically pure culture comprising a population of filamentous fungi of claim 1 and the chymosin secreted by the filamentous fungi.

* * * * *